(12) United States Patent
Mason et al.

(10) Patent No.: US 6,306,347 B1
(45) Date of Patent: Oct. 23, 2001

(54) OPTICAL SENSOR AND METHOD OF OPERATION

(75) Inventors: Richard W. Mason, Millis; Rudolf E. Slovacek, Norfolk; Kevin J. Sullivan, Medfield, all of MA (US)

(73) Assignee: Bayer Corporation, E. Walpole, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/010,096

(22) Filed: Jan. 21, 1998

(51) Int. Cl.$^7$ .................. G01N 21/01; G01N 33/487; G01N 33/52

(52) U.S. Cl. ............................. 422/58; 436/164

(58) Field of Search .................. 422/58; 436/164; 73/29.04

(56) References Cited

U.S. PATENT DOCUMENTS

| | | | |
|---|---|---|---|
| 2,761,417 | 9/1956 | Russell et al. | 118/410 |
| 3,992,158 | 11/1976 | Przybylowicz et al. . | |
| 4,003,707 | 1/1977 | Lübbers et al. . | |
| 4,042,335 | 8/1977 | Clément . | |
| 4,218,421 | 8/1980 | Mack, Jr. et al. | 422/66 |
| 4,356,149 | 10/1982 | Kitajima et al. | 422/56 |
| 4,476,870 | 10/1984 | Peterson et al. . | |
| 4,587,101 | 5/1986 | Marsoner et al. | 422/56 |
| 4,645,744 | 2/1987 | Charlton et al. | 436/74 |
| 4,649,123 | 3/1987 | Charlton et al. | 436/79 |
| 4,670,218 | 6/1987 | Gantzer et al. | 422/56 |

(List continued on next page.)

FOREIGN PATENT DOCUMENTS

| | | | |
|---|---|---|---|
| 0119861 | 11/1987 | (EP) | G01N/33/72 |
| 0333286 A1 | 9/1989 | (EP) . | |
| 0442276 | 8/1991 | (EP) | A61B/5/00 |
| 0142849 | 8/1992 | (EP) | G01N/33/52 |
| 0287328 | 10/1993 | (EP) | C07D/498/08 |
| 0287327 | 7/1994 | (EP) | C07D/498/08 |

(List continued on next page.)

OTHER PUBLICATIONS

Aartsma, T. et al., "Porphyrins.43. Triplet Sublevel Emission of Platinum Tetrabenzoporphyrin by Spectrothermal Principal Component Decomposition"; *J. Am. Chem. Soc.* 104, pp. 6278–6283 (after Jan. 1982).

Brandrup, J. et al., "Permeability and Diffusion Data" Polymer Handbook, 3rd edition, pp. VI/435–VI/449, John Wiley and Sons, New York, NY (1989), month not given.

(List continued on next page.)

*Primary Examiner*—Thomas P. Noland
(74) *Attorney, Agent, or Firm*—Weingarten, Schurgin, Gagnebin & Hayes LLP

(57) ABSTRACT

A multiple single use optical sensor includes a series of continuous sensor stripes deposited on a substrate web. At least one sample chamber is adapted to extend transversely across a discrete portion of the series of sensor stripes to facilitate analysis of a sample disposed therein. The sample chamber may be moved, or additional sample chambers provided to enable subsequent measurements of additional samples at unused discrete portions of the sensor stripes. The continuous nature of the sensor stripes provides consistency along the lengths thereof to enable calibration data obtained from one discrete portion of the sensor stripes to be utilized for testing an unknown sample an other discrete portion of the sensor stripes. This advantageously eliminates the need for any particular discrete portion of the sensor stripes to be contacted by more than one sample, for improved sensor performance.

12 Claims, 14 Drawing Sheets

U.S. PATENT DOCUMENTS

| | | | |
|---|---|---|---|
| 4,680,268 | 7/1987 | Clark, Jr. | 435/291 |
| 4,689,309 | 8/1987 | Jones | 436/95 |
| 4,716,363 | 12/1987 | Dukes et al. | 324/77 R |
| 4,734,375 | 3/1988 | Charlton | 436/74 |
| 4,752,115 | 6/1988 | Murray, Jr. et al. | |
| 4,781,890 | 11/1988 | Arai et al. | 422/56 |
| 4,806,491 | 2/1989 | Heim | 436/165 |
| 4,810,655 | 3/1989 | Khalil et al. | 436/138 |
| 4,824,789 | 4/1989 | Yafuso et al. | 436/68 |
| 4,857,472 | 8/1989 | Wolfbeis | 436/122 |
| 4,861,727 | 8/1989 | Hauenstein et al. | 436/136 |
| 4,895,156 | 1/1990 | Schulze | 436/172 X |
| 4,895,704 | 1/1990 | Arai et al. | 422/57 |
| 4,900,936 * | 2/1990 | Evers | 422/58 X |
| 4,919,891 | 4/1990 | Yafuso et al. | 422/58 |
| 4,974,929 | 12/1990 | Curry | |
| 5,011,779 | 4/1991 | Maimon | 435/293 |
| 5,030,420 | 7/1991 | Bacon et al. | 422/82.07 |
| 5,043,286 | 8/1991 | Khalil et al. | 436/136 |
| 5,047,350 | 9/1991 | Switalski et al. | 436/136 |
| 5,075,127 | 12/1991 | Yafuso et al. | 427/2 |
| 5,081,041 | 1/1992 | Yafuso et al. | 436/68 |
| 5,081,042 | 1/1992 | Yafuso et al. | 436/68 |
| 5,091,800 | 2/1992 | Offenbacher et al. | 359/350 |
| 5,112,768 * | 5/1992 | Lerner | 73/29.04 X |
| 5,127,405 | 7/1992 | Alcala et al. | |
| 5,173,432 | 12/1992 | Lefkowitz et al. | 436/138 |
| 5,190,729 | 3/1993 | Hauenstein et al. | 422/91 |
| 5,208,147 | 5/1993 | Kagenow et al. | 435/14 |
| 5,281,825 | 1/1994 | Berndt et al. | 250/458.1 |
| 5,298,144 | 3/1994 | Spokane | 204/403 |
| 5,326,531 | 7/1994 | Hahn et al. | 422/82.06 |
| 5,341,805 | 8/1994 | Stavridi et al. | 356/39 X |
| 5,348,861 * | 9/1994 | Kulla | 73/29.04 X |
| 5,352,348 | 10/1994 | Young et al. | 204/153.12 |
| 5,387,329 | 2/1995 | Foos et al. | 204/415 |
| 5,387,525 | 2/1995 | Munkholm | 436/111 |
| 5,397,538 | 3/1995 | Stark et al. | 422/57 |
| 5,453,248 | 9/1995 | Olstein | 422/82.07 |
| 5,462,858 | 10/1995 | Bale Oenick et al. | 435/16 |
| 5,462,879 | 10/1995 | Bentsen | 436/136 |
| 5,464,777 | 11/1995 | Yip | 436/98 |
| 5,494,562 | 2/1996 | Maley et al. | 204/403 |
| 5,506,148 | 4/1996 | Munkholm | 436/111 |
| 5,520,883 | 5/1996 | Charlton et al. | 422/56 |
| 5,601,694 | 2/1997 | Maley et al. | 204/415 |
| 5,605,152 | 2/1997 | Slate et al. | 128/634 |
| 5,624,847 | 4/1997 | Lakowicz et al. | 438/68 |
| 5,631,340 | 5/1997 | Olstein | 528/59 |
| 5,863,460 * | 1/1999 | Slovacek et al. | 252/301.35 |

FOREIGN PATENT DOCUMENTS

| | | | |
|---|---|---|---|
| 0646784 A1 | 4/1995 | (EP) | |
| 1485506 | 9/1977 | (GB) | |
| 87/00023 | 1/1987 | (WO) | A61B/5/00 |
| 90/07107 | 6/1990 | (WO) | G01N/21/64 |
| 92/19957 | 11/1992 | (WO) | G01N/21/76 |
| 95/10522 | 4/1995 | (WO) | C07D/487/22 |
| 95/26501 | 10/1995 | (WO) | G01N/31/22 |
| 95/30148 | 11/1995 | (WO) | G01N/31/22 |
| 97/33519 | 9/1997 | (WO) | |
| 97/37210 | 10/1997 | (WO) | G01N/21/64 |

OTHER PUBLICATIONS

Bruno, et al., "All–Solid–State Miniaturized Fluorescence Sensor Array for the Determination of Critical Gases and Electrolytes in Blood" *Anal. Chem.* 69, pp. 507–513 No. 3, Feb. 1997.

Demas, J. et al., "Design and Applications of Highly Luminescent Transition Metal Complexes"; *Analytical Chemistry*, vol. 63, No. 17; pp. 829A–837A, Sep. 1991.

Kautsky, V. et al., "Nachweis geringster Sauerstoffmengen durch Phosphoreszenztilgung", *Zeitschrift fir anaorganische und allgemeine Chemie. Band* 222, pp. 126–134 (German) Jan. 1935.

Kautsky, V. et al., "Luminescenzumwandlung durch Sauerstoff Nachweis geringster Sauerstoffmengen", *Zeitschrift Naturforschung* 2a, pp. 167–172 (1947). (German) month not given.

Klimant, I. et al., "Oxygen–Sensitive Luminescent Materials Based on Silicone–Soluble Ruthenium Diimine Complexes" *Anal. Chem.* 67 pp. 3160–3166 No. 18, Sep. 1995.

Lui, Hsue–Yang et al., "Oxygen Permeability of Sol–Gel Coatings", *Applied Spectroscopy*, vol. 46, No. 8 pp. 1266–1272 (1992). After February.

Papkovsky et al., "Phosphorescent Complexes of Porphyrin Ketones: Optical Properties and Application to Oxygen Sensing", *Anal. Chem.* 67, pp. 4112–4117 No. 22, Nov. 1995.

Papkovsky et al., "Phosphorescent Polymer Films for Optical Oxygen Sensors", *Biosensors & Electronics* 7, pp 199–206 (1991), after May.

Roffey, "Photopolymerization of Surface Coatings", *Wiley–Interscience,* p. 110–117 (1985) month not given.

Salame, M. "Transport Properties of Nitrile Polymers", *J. Polymer Sci. Symp.* 41, pp 1–15 (1973) month not given.

Stern, V. et al., "Uber die Abklingungszeit der Fluoresenz", *Physik. Zeitschr.* XX; pp. 183–188 (1919). (German) Jan.

Vinogradov et al., "Metallotetrabenzoporphyrins. New Phosphorescence Probes for Oxygen Measurements", *J. Chem. Soc. Perkin Trans.* 2, pp. 103–111 (1995), month not given.

Watts, R.J. et al., "Spectroscopic Characerization of Complexes of Ruthenium (II) and Iridium (III) with 4,4'–Diphenyl–2,2'–bipyridine and 4,7–Diphenyl–1,10–phenanthroline", *J. Am. Chem. Soc.,* pp. 3184–3188 93:13 Jun. 1971.

Yang et al., "Oxygen Permeability Coefficients of Polymers for Hard and Soft Contact Lens Applications", *J. Membrane Sci.* 9, pp. 53–67 (1981) after Jan.

Optical Chemicals Sensors Based on Sol–Gel Materials: Recent Advances and Critical Issues; B.D. MacCraith, C. McDonagh, A.K. McEvoy, T. Butler, G. O'Keefe and V. Murphy; Journal of Sol–Gel Science Technology 8; pp. 1053–1061; 1997, month not given.

* cited by examiner

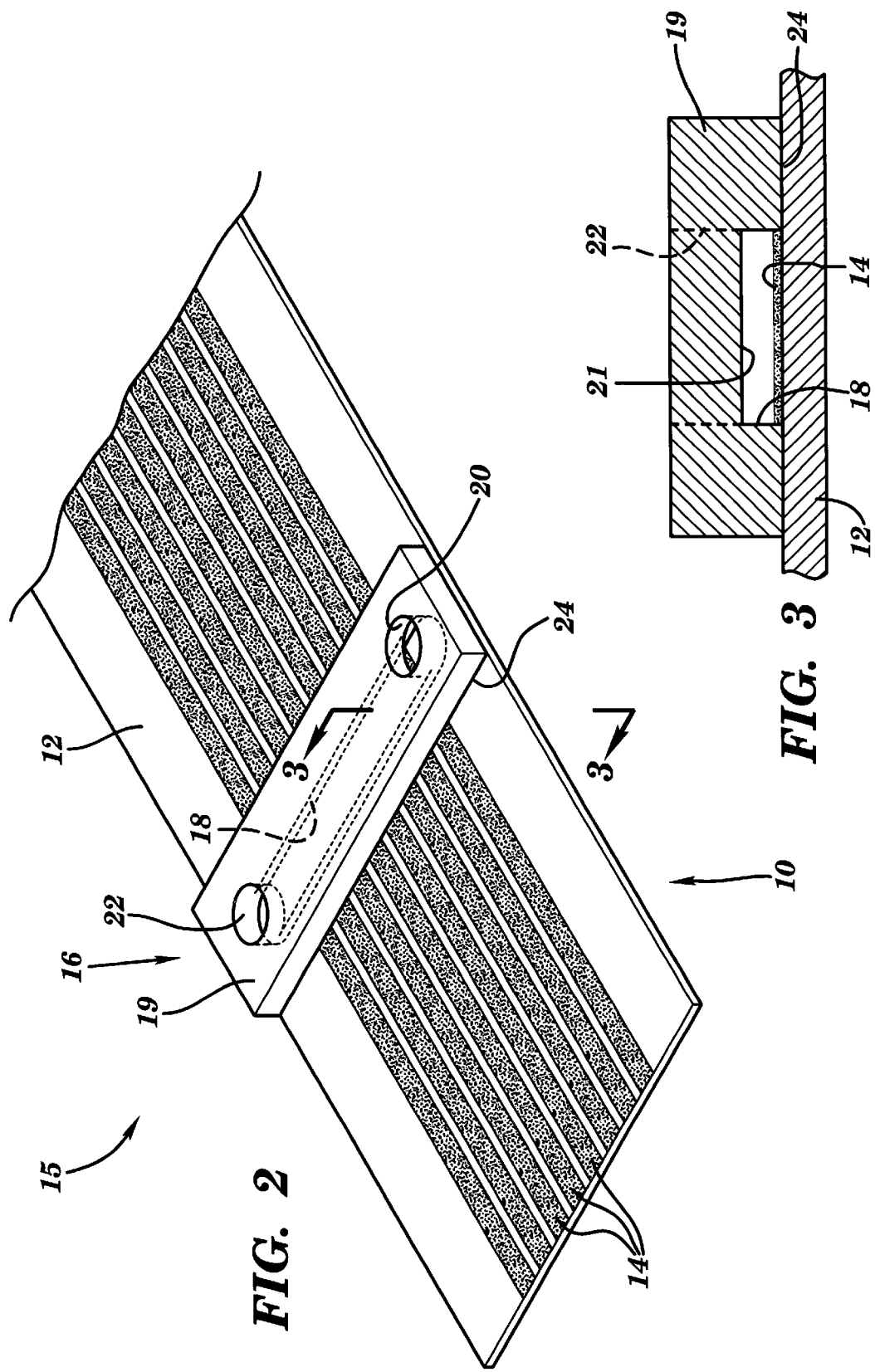

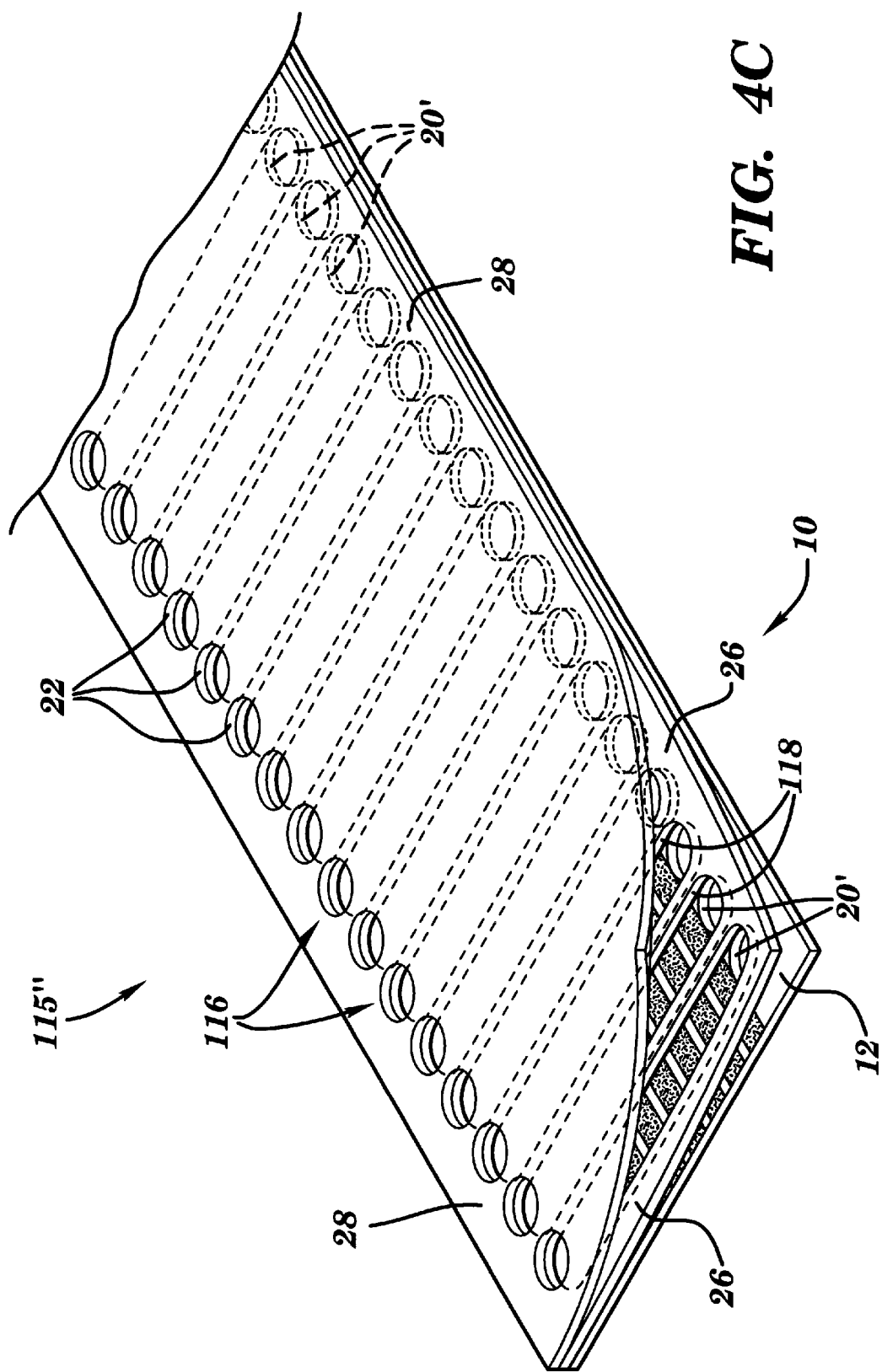

OPTICAL SENSOR AND METHOD OF OPERATION

BACKGROUND OF THE INVENTION

1. Field of the Invention

This invention relates to chemical analysis of liquids, and more particularly, to an optical sensor for sensing analyte content of biological fluids such as blood.

2. Background Information

Chemical analysis of liquids, including biological fluids such as blood, plasma or urine is often desirable or necessary. Sensors that utilize various analytical elements to facilitate liquid analysis are known. These sensing elements have often included a reagent in either a wet or dry form sensitive to a substance or characteristic under analysis, termed analyte herein. The reagent, upon contacting a liquid sample containing the analyte, effects formation of a colored material or another detectable change in response to the presence of the analyte. Examples of dry analytical sensing elements include pH test strips and similar indicators wherein a paper or other highly absorbent carrier is impregnated with a material, chemically reactive or otherwise, that responds to contact with liquid containing hydrogen ion or other analyte and either generates color or changes color. Specific examples of such test strips are disclosed in European publication No. EP 0119 861 B1, which describes a test for bilirubin; in U.S. Pat. No. 5,462,858 which describes a dry multilayer strip for measuring transaminase activity; and U.S. Pat. No. 5,464,777 which discloses a reflectance based assay for creatinine. While providing a convenience factor, in that they can be stored dry and are ready to use on demand, these individual test elements are generally utilized in "wet" blood or serum chemistry, wherein the strips become saturated during use. This hydration and the depletion of reactive chemical reagents effectively prevents their re-use. This aspect also complicates handling and disposal of the multitude of individual used test elements.

Alternatively, some analytes can be measured with a sensing element which is used repeatedly after an initial wet-up and calibration and with washes between samples. For example a reuseable electrochemical sensor for oxygen is described in commonly assigned U.S. Pat. No. 5,387,329 and a reuseable electrochemical sensor for glucose is described in commonly assigned U.S. Pat. No. 5,601,694. These sensors function within the context of a complex piece of support instrumentation to perform the repetitive calibration and wash functions.

Other analytical sensing elements which are based on an optical signal response are disclosed in U.S. Pat. Nos. 4,752,115; 5,043,286; 5,453,248 and by Papkovsky et al in Anal. Chem. vol 67 pp 4112–4117 (1995) which describe an oxygen sensitive dye in a polymer membrane, as does commonly assigned U.S. patent application Ser. No. 08/617,714, now U.S. Pat. No. 5,863,460 which is hereby incorporated in its entirety, herein. Examples of an optical $CO_2$ sensor are described in U.S. Pat. Nos. 4,824,789; 5,326,531 and 5,506,148. These elements utilize a polymer based membrane chemistry to achieve advantages in storage, and continuous use or re-use as compared to the wetable or hydrated single use chemistry strips. Analytical elements of this type are typically adapted for multiple uses within a single sample chamber of an optical sensor assembly. In operation, a fluid sample of unknown analyte content (an "unknown sample") is tested by inserting the sample into the sample chamber where it contacts the analytical element. A change in the optical properties of the analytical element is observed. Such an observation is then compared to calibration data previously obtained by similarly testing a calibration liquid of known analyte content. In this manner, characteristics of the analyte of interest in the unknown sample are determined.

An example of a single use optical sensor application of this normally reuseable type is known as a "AVL OPTI 1" available from AVL List GmbH of Graz, Austria. While sensors of this type may operate satisfactorily in many applications, they are not without limitations. In particular, they rely on sequential steps for calibration and subsequent sample readings, in which each such sensing device must be individually calibrated prior to testing an unknown sample. This technique is required due to variations in analytical elements from sensor to sensor. These variations may be attributed to a variety of factors, including manufacturing variables such as differences in individual lots, and distinct storage histories.

Sequential calibration and sample reading may problematically lead to sample contamination in the event the sample chamber and analytical elements are insufficiently washed between samples. In addition, the calibration is time consuming and may delay analysis of the unknown sample. This delay may be particularly inconvenient in some operating environments such as, for example, critical care facilities.

An additional disadvantage of the sequential approach is the temporal variation or time delay between testing of the calibrant and testing of the unknown sample. This variation may provide a potential opportunity for inaccuracies in test results.

Further, discarded wash fluid comprises approximately 80% of the waste generated by such conventional sensor based testing techniques. This waste is classified as biohazardous particularly if it is co-mingled with biological samples and thus disposal thereof is relatively expensive, both in economic and environmental terms. This waste also poses a potential health risk to health care workers and those who may otherwise come into contact with the waste during or after disposal.

Thus, a need exists for an improved optical sensor that eliminates the need for serial calibration and addresses the problems of waste generation inherent in sensor practices of the prior art while retaining the advantages of disposable, use on demand, devices.

SUMMARY OF THE INVENTION

According to an embodiment of the present invention, an optical sensor adapted for sensing analyte content of a plurality of samples is provided. The optical sensor comprises:

- a substrate web of predetermined length, the substrate web being substantially gas impermeable and optically transparent in a predetermined spectral range;
- a plurality of elongated sensor stripes extending in a parallel spaced relation along the length of the web;
- each one of the plurality of sensor stripes adapted for providing an optically discernible response to presence of at least one analyte;
- the optical sensor adapted for selective analyte-sensing contact with the plurality of samples, wherein each one of the plurality of samples are selectively superimposable with each one of the plurality of elongated sensor stripes at one of a plurality of discrete positions along the lengths thereof;
- the optically discernible response being substantially identical at a plurality of discrete positions along the length thereof.

In a first variation of this aspect of the present invention, an optical sensor assembly adapted for sensing analyte content of a plurality of samples is provided. The optical sensor assembly comprises:

- the optical sensor as set forth in the above-referenced first aspect of the present invention;
- at least one sample chamber selectively superimposable with each of the plurality of elongated sensor stripes at the plurality of discrete positions along the lengths thereof;
- wherein the at least one sample chamber is adapted for alternately maintaining individual ones of the plurality of samples in the analyte-sensing contact.

In a second variation of the first aspect of the present invention, an optical sensor assembly adapted for sensing analyte content of a plurality of samples is provided. The optical sensor assembly includes:

- the optical sensor as set forth in the above-referenced first aspect of the present invention;
- a plurality of sample chambers disposed in parallel, spaced relation on the web, each one of the plurality of sample chambers being sealably superposed with the plurality of elongated sensor stripes at one of a plurality of discrete positions along the lengths thereof;
- wherein each of the plurality of sample chambers is adapted for alternately maintaining individual ones of the plurality of samples in the analyte-sensing contact.

In a second aspect of the present invention, a method of operating an optical sensor comprises the steps of:

(a) providing an optical sensor including:
   i) a substrate web of predetermined length, the substrate web being substantially gas impermeable and optically transparent in a predetermined spectral range;
   ii) a plurality of elongated sensor stripes extending in parallel, spaced relation along the length of the web, each one of the plurality of sensor stripes adapted for providing an optically discernible response to presence of at least one of a plurality of discrete analytes;
   iii) the optical sensor adapted for selective analyte-sensing contact with the plurality of samples, wherein each one of the plurality of samples are selectively superimposable with each one of the plurality of elongated sensor stripes at one of a plurality of discrete positions along the lengths thereof;
   iv) the optically discernible response being substantially identical at a plurality of discrete positions along the length thereof;
   v) wherein the plurality of samples comprises at least one unknown sample and at least one calibration sample, the optical sensor adapted for being calibrated upon disposition of the calibration sample in the analyte-sensing contact with the optical sensor at a discrete position along the length of the sensor stripes distinct from that of the at least one unknown sample;
(b) placing the calibration sample in the analyte-sensing contact with the optical sensor at one of the plurality of discrete positions along the lengths of the sensor stripes;
(c) measuring optical response of the optical sensor at the one of the plurality of discrete positions;
(d) obtaining calibration data utilizing the optical response of the one of the plurality of discrete positions;
(e) placing the at least one unknown sample in the analyte-sensing contact with the optical sensor at an other of the plurality of discrete positions along the lengths of the sensor stripes;
(f) measuring optical response of the other of the plurality of discrete positions;
(g) utilizing the calibration data obtained for the one of the plurality discrete positions for calibration of the optical response of the other of the plurality of discrete positions.

The above and other features and advantages of this invention will be more readily apparent from a reading of the following detailed description of various aspects of the invention taken in conjunction with the accompanying drawings.

BRIEF DESCRIPTION OF THE DRAWINGS

FIG. 2 is a perspective view of an embodiment of an optical sensor assembly of the present invention, including the optical sensor of FIG. 1 and a sample chamber disposed thereon;

FIG. 3 is a cross-sectional elevational view taken along FIG. 3—3 of FIG. 2;

FIG. 4C is a view similar to FIGS. 4A and 4B, of a further alternate embodiment of an optical sensor assembly of the present invention;

DETAILED DESCRIPTION OF THE PREFERRED EMBODIMENTS

Figure 1:
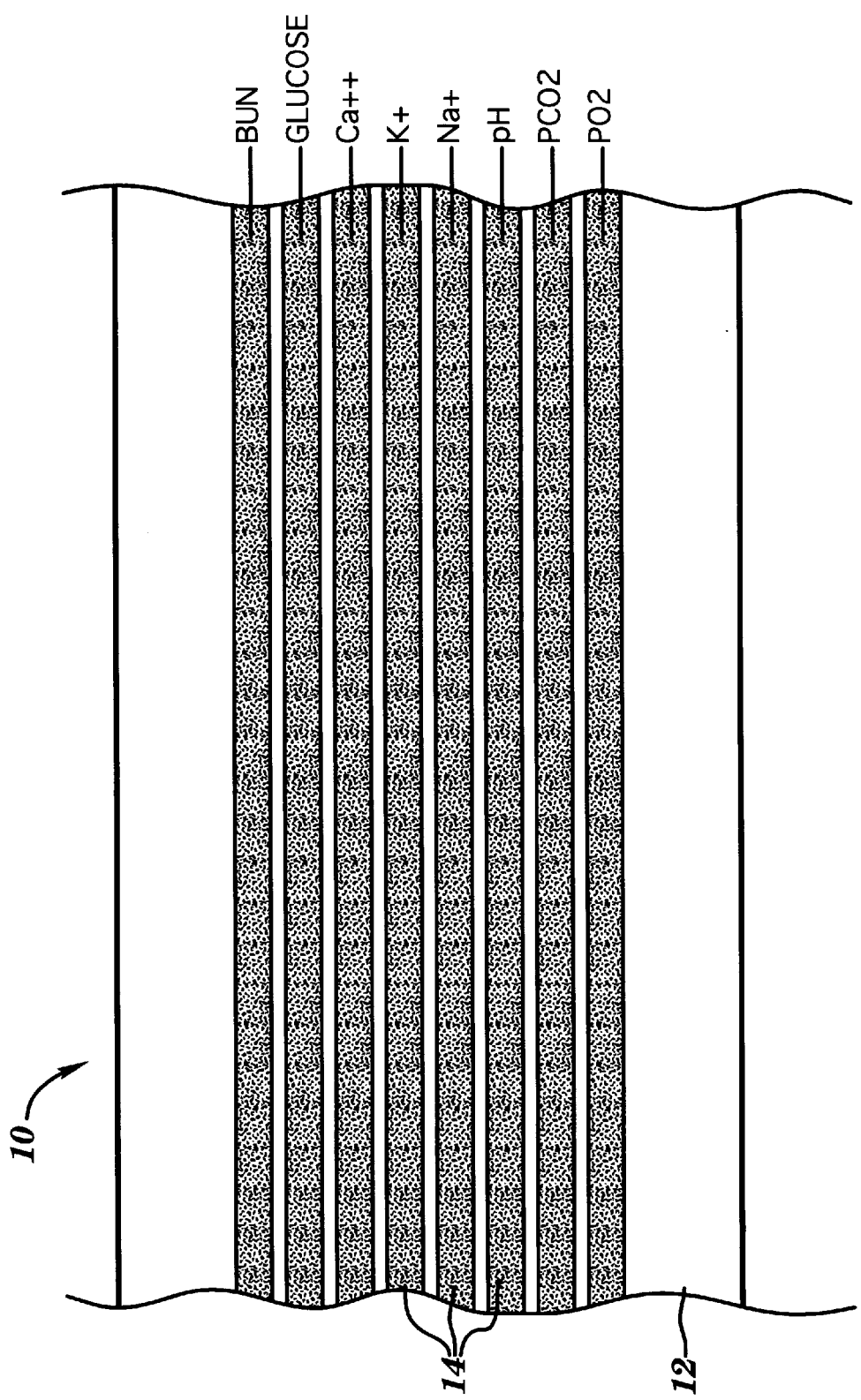
FIG. 1 is a plan view of an optical sensor of the present invention.

Referring to the figures set forth in the accompanying drawings, illustrative embodiments of the present invention will be described in detail hereinbelow. For clarity of exposition, like features shown in the accompanying drawings shall be indicated with like reference numerals and similar features shown, for example, in alternate embodiments in the drawings, shall be indicated with similar reference numerals.

Briefly described, the present invention includes a multiple single use optical sensor fabricated as a series of continuous sensor stripes 14 deposited on a substrate web 12 (FIG. 1). One sample chamber 16 (FIG. 2) or multiple sample chambers 116 (FIG. 4) are adapted to extend transversely across a discrete portion of the series of sensor stripes 14 to facilitate analysis of a sample disposed therein. Sample chamber 16 may be moved, or additional sample chambers utilized to enable subsequent measurements of additional samples at unused discrete portions of sensor stripes 14. The continuous nature of the sensor stripes provides consistency along the lengths thereof to enable calibration data obtained from one discrete portion of a sensor stripe 14 to be utilized for testing and determining presence and concentration of analytes in an unknown sample disposed at an other discrete portion of the sensor stripe. This aspect advantageously eliminates the need for any particular discrete portion of a sensor stripe 14 to be contacted by more than one sample for improved sensor performance and reduced waste.

Throughout this disclosure, the term "analyte" shall refer to any substance, compound, or characteristic such as, for example, pH, capable of detection and/or measurement relative to a liquid sample. Similarly, the term "concentration" shall refer to the level or degree to which an analyte is present in a sample. The term "axial" or "longitudinal" when used in reference to an element of the present invention, shall refer to the relatively long dimension or length thereof. For example, when used in connection with an optical sensor of the present invention, "longitudinal" shall refer to a direction substantially parallel to sensor stripes 14 thereof. Similarly, the term "transverse" shall refer to a direction substantially orthogonal to the axial or longitudinal direction. Moreover, the use of the term "calibration" or "calibration sample" shall be understood to encompass a sample of substantially any known analyte composition, including "QC" or "quality control" samples commonly used by those skilled in the art to help ensure uniformity between tests.

Referring now to the drawings in detail, as shown in FIG. 1, an optical sensor 10 of the present invention includes a backing or substrate web 12, with a plurality of sensor stripes 14 extending longitudinally in parallel, spaced relation thereon. Backing web 12 is fabricated as a sheet from a material optically transparent in a predetermined optical spectrum, as will be discussed hereinafter. The backing web is preferably fabricated from a substantially liquid and gas impermeable material, such as, for example, glass or a thermoplastic material such as polyethylene terephthalate or SARAN®.

In this regard, those skilled in the art will recognize that fabrication of the substrate web from relatively gas permeable materials, such as, for example, Polytetrafluoroethylene (PTFE), may disadvantageously distort analyte analysis. This is due to the tendency for analytes to diffuse out of the sample, or for ambient gases such as atmospheric Oxygen ($O_2$) and/or Carbon Dioxide ($CO_2$), to leach out of the substrate and into the sensor material and sample, during analysis. In a preferred embodiment, substrate web 12 is fabricated as a film of polymeric plastic material sold under the Dupont trademark Mylar®. Webs were obtained from ERA Industries INC. in Seabrook N.H. In addition to being substantially gas impermeable, this material advantageously provides substrate web 12 with flexibility, as will be discussed in greater detail hereinafter. The substrate web may be fabricated using any convenient method common in the art, such as conventional molding, casting, extrusion or other suitable thin-film fabrication techniques.

Each sensor stripe 14 may be fabricated as a series of discrete portions, such as a series of dots, arranged in a row extending longitudinally along the substrate web. Alternatively, in a preferred embodiment as shown, each sensor stripe 14 extends substantially continuously in the longitudinal direction. Each sensor stripe 14 comprises at least one of any number of analytical elements, including substances, compounds or structures known to those skilled in the art to be optically sensitive to a predetermined analyte. Such optical sensitivity may include, for example, exhibition of optically discernible changes in reflectance, refractive index, light transmittance, or in a preferred embodiment, luminescence, which may encompass emitted light in the form of either phosphorescence or fluorescence.

Examples of analytes that may be analyzed include BUN (blood urea nitrogen), glucose, calcium ($Ca^{++}$), potassium ($K^+$), sodium ($Na^+$), pH, and partial pressures of carbon dioxide ($pCO_2$) and oxygen ($pO_2$). Preferred analytical elements include, for example, analytical elements for carbon dioxide ($pCO_2$) as disclosed in U.S. Pat. Nos. 5,387,525 (the '525 patent) and 5,506,148 (the '148 patent), an analytical element for pH as disclosed in International Publication No. WO 95/30148 and by Bruno, et al. in Anal. Chem. Vol 69, pp. 507–513 (1997) and an analytical element for oxygen (pO2) as disclosed in U.S. patent application Ser. No. 08/617,714, all of which are hereby incorporated by reference in their entireties, herein. All of these preferred analytical elements emit characteristic luminescence which is responsive to the presence of their respective analytes when subjected to incident light of a predetermined spectral wavelength or spectral range.

In a preferred embodiment, each sensor stripe 14 comprises a single analytical element. However, it is contemplated that a single sensor stripe of the present invention may comprise a plurality of analytical elements, each of the plurality of analytical elements exhibiting an independently measurable response to presence of their respective analytes. In this regard, for example, a single sensor stripe 14 may comprise first, second and third analytical elements. The first analytical element may exhibit enhanced fluorescence in presence of a first analyte when subjected to incident light in a first spectral range. The second analytical element may exhibit diminished phosphorescence in presence of a second analyte when subjected to incident light in a second spectral range. The third analytical element may, for example, exhibit another optical response, such as enhanced reflectance, in presence of a third analyte when subjected to incident light in a predetermined spectral range.

Sensor stripes 14 are applied to the substrate web 12 by any convenient means, either by batch or continuous processes. For example, stripes 14 may be applied by conventional printing techniques, such as silk screen or other lithographic techniques. It is also contemplated that laser or ink jet printing technologies may ultimately be adapted for application of the sensor stripes. Alternatively, the stripes may be applied by continuous direct deposition or painting-type application techniques as well as by spray painting.

For example, in a preferred embodiment, one may use a micro dispensing system of the type commercially available from Gilson, Worthington, Ohio; Cavro Scientific Instruments Inc., Sunnyvale, Calif.; Elder Laboratories Inc., Napa, Calif.; IVEK Corp., Springfield, Vt.; or Fluid Metering Inc., Oyster bay, N.Y., as well as other commercial sources for chromatographic delivery systems. Operation of this equipment is familiar to those of skill in the art. Briefly described, the material comprising the sensor stripe, including at least one analytical element, is prepared in liquid form and fed to a nozzle of predetermined size and shape, suspended or superposed over substrate web 12. The liquid is expressed from the nozzle at a predetermined rate onto the substrate web as the web is moved longitudinally at a predetermined rate relative the nozzle with either reciprocating or rolled web technologies of a more continuous nature. This process is repeated at spaced locations along the transverse dimension or width of the substrate web for each sensor stripe. The liquid is then dryed or cured in a conventional manner to form a solid sensor stripe 14.

While the aforementioned method for deposition of sensor stripes 14 is preferred, substantially any method of deposition may be utilized that enables the mechanical and optical properties of sensor stripes 14 to be held substantially constant over the lengths thereof. In this regard, parameters such as stripe thickness, width, contour, and composition are maintained at predetermined levels to provide sensor response that is relatively constant or identical at various positions along the length of each sensor stripe 14. Moreover, the skilled artisan will recognize that sensor response will be particularly consistent over relatively short sections of the stripe. In other words, the uniformity of response of discrete portions of a sensor stripe 14 will be in some measure proportional to the spatial distance therebetween.

Referring now to FIG. 2, an optical sensor assembly 15 of the present invention includes a sample chamber 16 adapted for use in combination with optical sensor 10. Sample chamber 16 comprises an elongated, substantially tubular cavity 18 disposed within an elongated chamber member 19. Cavity 18 has a transverse cross-section nominally uniform along the length thereof and defined, in part, by a substantially concave or recessed surface 21, best shown in FIG. 3. Throughout this disclosure, the term "concave" shall refer to any substantially hollowed out recess or cavity, regardless of whether the surface thereof is curved or comprises a plurality of substantially flat surfaces as shown herein. In this regard, referring to FIG. 3, concave surface 21 extends inwardly from a substantially planar engagement surface 24 of chamber member 19.

As shown in FIGS. 2 and 3, engagement surface 24 is adapted for being superimposed transversely across, preferably in slidable, surface-to-surface engagement with substrate web 12 and sensor stripes 14. So disposed, a discrete portion of web 12, including portions of sensor stripes 14, effectively closes concave surface 21, to thus define a longitudinal side wall of tubular cavity 18. Moreover, engagement surface 24, substrate web 12 and sensor stripes 14 are each sufficiently smooth that upon application of a predetermined force tending to maintain such surface-to-surface contact, a fluid-tight seal is maintained therebetween. Sample chamber 16 is thus adapted for supportably maintaining a fluid sample in surface to surface or analyte-sensing contact with a discrete portion of each sensor stripe 14, as will be discussed in greater detail hereinafter with respect to operation of the embodiments of the present invention.

As shown in FIG. 2, entry and exit apertures 20 and 22, respectively, each extend through chamber member 19. The apertures each extend orthogonally to, and in communication with, cavity 18 at opposite ends thereof, to facilitate sample flow into and out of sample chamber 16.

As shown, sample chamber 16 is a reusable device, adapted for either multiple tests at a particular discrete location on sensor stripes 14, or alternatively, progressive movement to fresh (unused) portions of the sensor stripes for successive sample testing. These alternative testing techniques will be discussed hereinafter with respect to operation of the present invention.

Figure 4A:
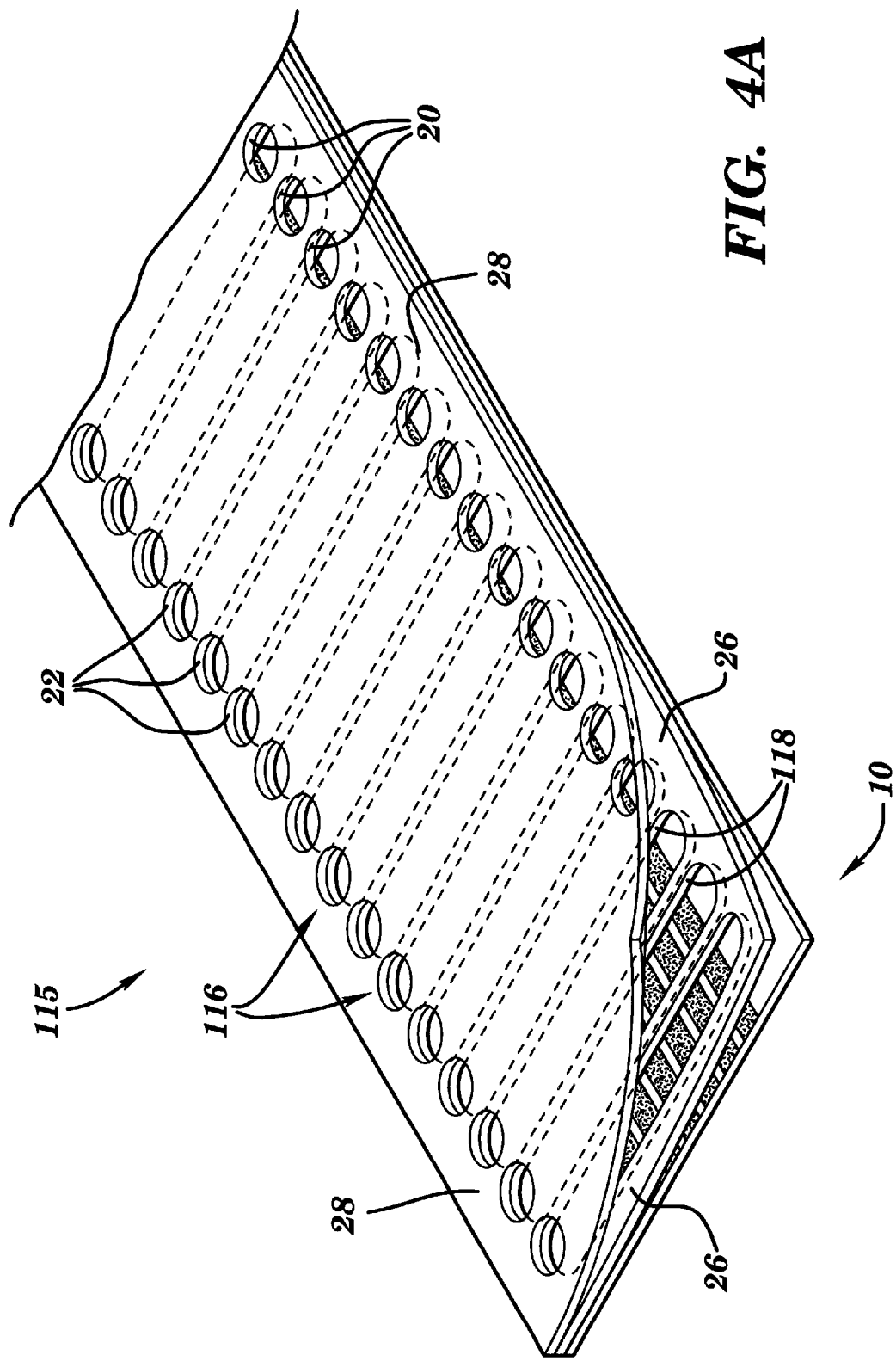
FIG. 4A is a perspective view, with portions thereof peeled back, of an alternate embodiment of an optical sensor assembly of the present invention, including the optical sensor of FIG. 1 and a plurality of sample chambers disposed thereon.

Referring now to FIG. 4A, an alternate embodiment of the present invention is shown as optical sensor assembly 115. This optical sensor assembly includes multiple individual sample chambers 116 disposed on optical sensor 10. Sensor assembly 115 is preferably fabricated as a laminate comprising optical sensor 10, an intermediate or chamber web 26 and a cover web 28.

Chamber web 26, in combination with cover web 28, comprise sample chambers 116. As shown, chamber web 26 is an elongated sheet that includes a series of transversely extending cavities 118. The cavities are spaced at predetermined distances from one another along the length of the web.

Web 26 is preferably fabricated from a material and in a manner similar to that of substrate web 10. Cavities 118 are formed by any convenient method, such as, for example, by subjecting web 26 to conventional die-cutting operations. Alternatively, in the event web 26 is fabricated by molding, cavities 118 may be molded integrally therewith.

Cover web 28 is superimposed or laminated in a sealed, fluid-tight manner over chamber web 26. This combination of chamber web 26 and cover web 28 effectively provides each chamber 116 with a transverse cross-section defined by concave surface 21 as described hereinabove with respect to FIG. 3. A series of entry and exit bores or apertures 20 and 22 extend through cover web 28 in communication with opposite ends of cavities 118 as also discussed hereinabove. Alternatively, the bores or apertures 20 and 22 may also be formed in the substrate web itself 12 or used in combination with apertures in the cover web 28. Cover web 28 is preferably fabricated from a material and in a manner similar to that of both substrate web 12 and chamber web 26. Any conventional means, including, for example, ultrasonic and vibration welding or adhesives of various types may be utilized to laminate cover web 28 to chamber web 26. In a preferred embodiment, however, a conventional adhesive is utilized to bond webs 26 and 28 to one another.

Chamber web 26 is laminated onto optical sensor 10 so that sensor 10 effectively closes and seals concave surfaces 21 of each cavity 118 in a manner similar to that described hereinabove with respect to cavity 18. Thus, rather than being movable as is cavity 18 described hereinabove, cavities 118 are preferably immovably or permanently disposed at spaced intervals along the length of optical sensor 10. The manner in which chamber web 26 is laminated onto optical sensor 10 is similar to that in which chamber web 26 is bonded to cover web 28.

Figure 4B:
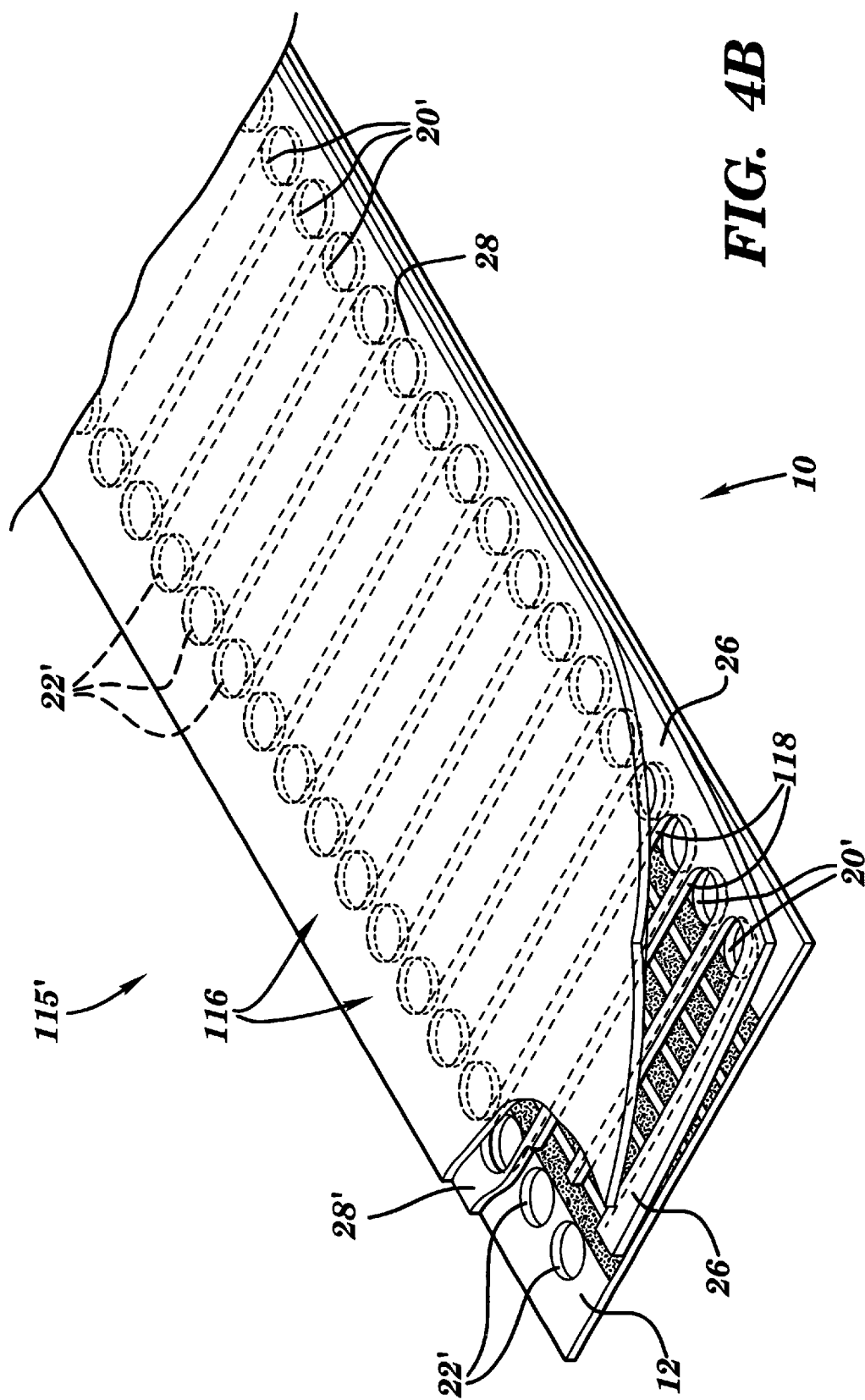
FIG. 4B is a view similar to FIG. 4A, of another alternate embodiment of an optical sensor assembly of the present invention.

Turning now to FIG. 4B, a further alternate embodiment is shown as optical sensor assembly 115'. Assembly 115' is substantially similar to optical sensor assembly 115, with the distinction that entry and exit apurtures 20' and 22' are disposed in substrate web 12, rather than in web 28.

An additional, similar alternative embodiment is shown in FIG. 4C as optical sensor assembly 115". In assembly 115", some of the entry and exit apertures (i.e. exit apertures 22 as shown) are disposed in web 28 while others of the entry and exit apertures (i.e. entry apertures 20') are disposed in substrate web 12.

Figure 9:
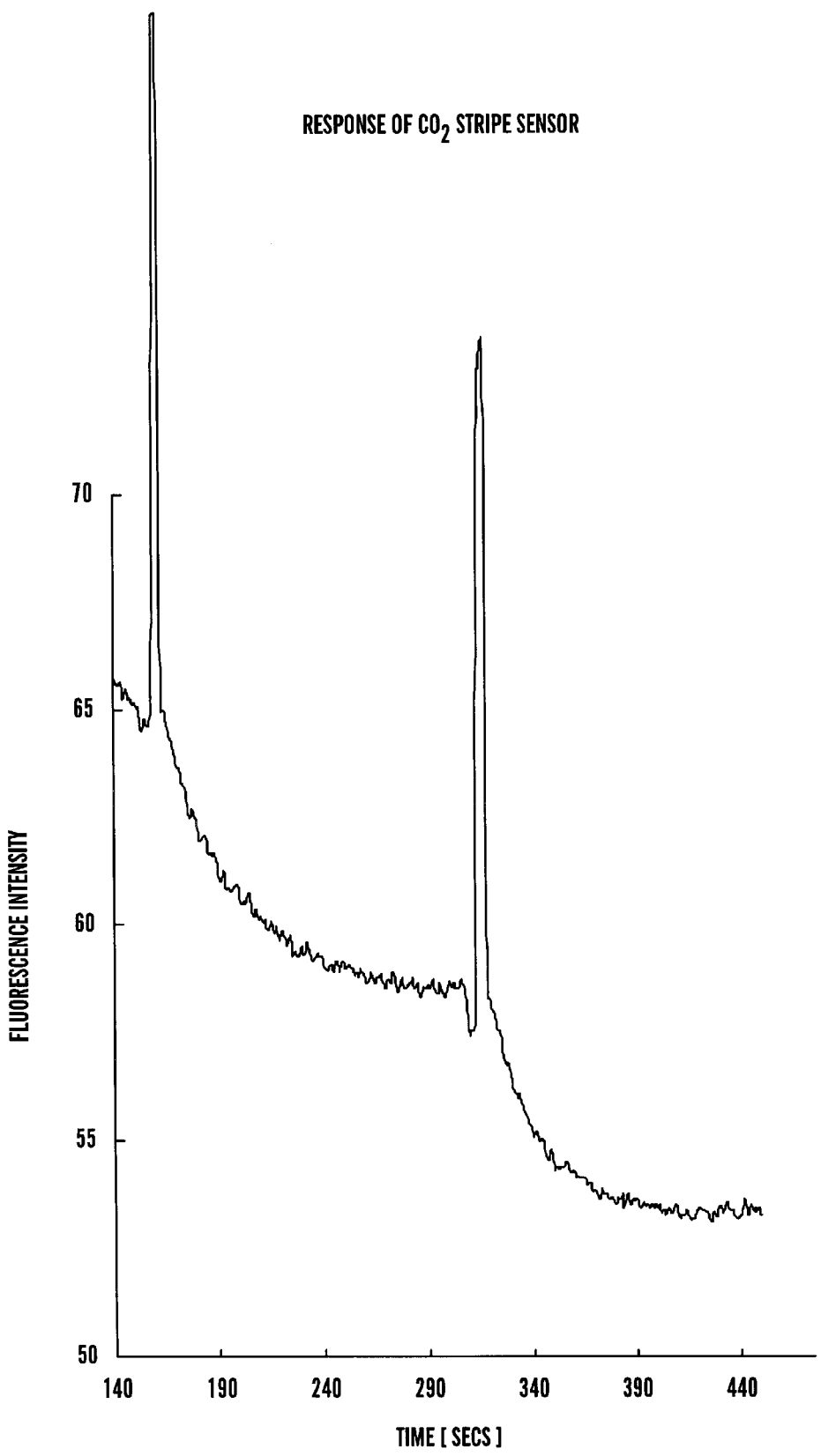
FIG. 9 is a response curve similar to that of FIG. 7B, for a carbon dioxide sensing portion of an optical sensor of the type shown in FIGS. 1 and 4.
Figure 10:
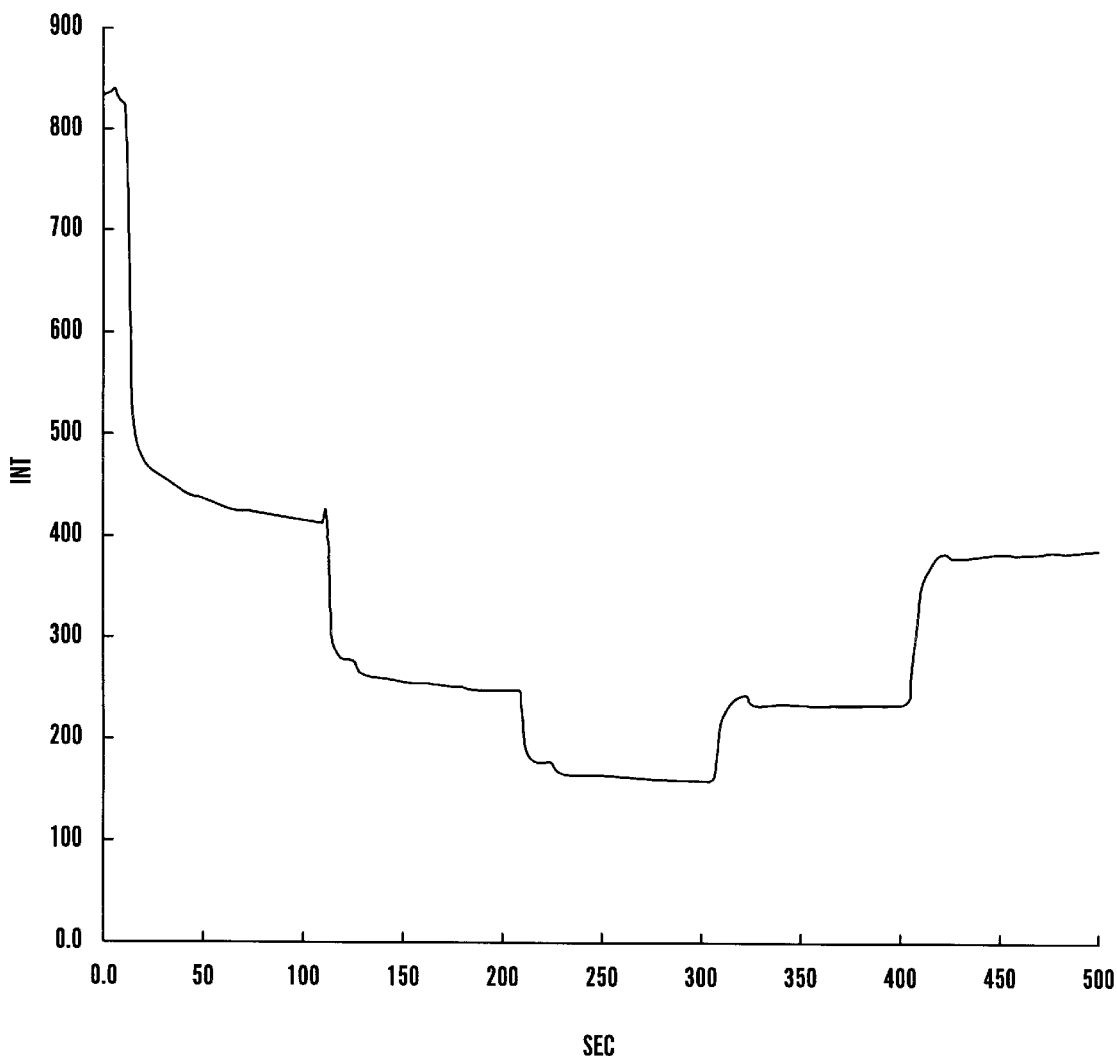
FIG. 10 is a graphical representation of response to acidification of the fluorescein dye, of the portion of the optical pH sensor described in FIGS. 1 and 4.

Preferred embodiments of the invention having been described, the following is a description of the operation thereof. Referring initially to optical sensor assembly 15, as shown in FIGS. 2 and 3, a sample to be tested is inserted into entry aperture 20, such as by a pump means (not shown but which may include the use of capillary forces or negative or postive pressures). The sample is inserted until it substantially fills sample chamber 16 and is thus placed in analyte-sensing contact with a discrete portion of each respective sensor strip 14 as discussed hereinabove. Once so disposed, any of a variety of suitable instruments may be utilized to measure optical response of the discrete portions to determine the existence and/or concentration of analytes in the sample. Examples of such instrumentation include a commercially available fluorimetric device known as a model LS50-b Spectrofluorimeter available from Perkin Elmer Corporation of Norwalk, Conn. A solid sample holder accessory was specifically modified to accept the striped film sensors for front face fluorescence measurements. By "front face" or "front surface" it is meant that excitation and emission collection is off the same surface. Illumination and collection optics permit transmission of the excitation and emission signals through the Mylar® substrate. Samples were introduced into a hollowed out aluminum sample chamber located on the side of the Mylar® opposite from the illumination and collection optics and with the opening covered by the sensor stripe so that samples contacted the stripe directly. Sample measurements with this device are provided in Example 6 (FIG. 9) and Example 8 (FIG. 10).

Figure 5:
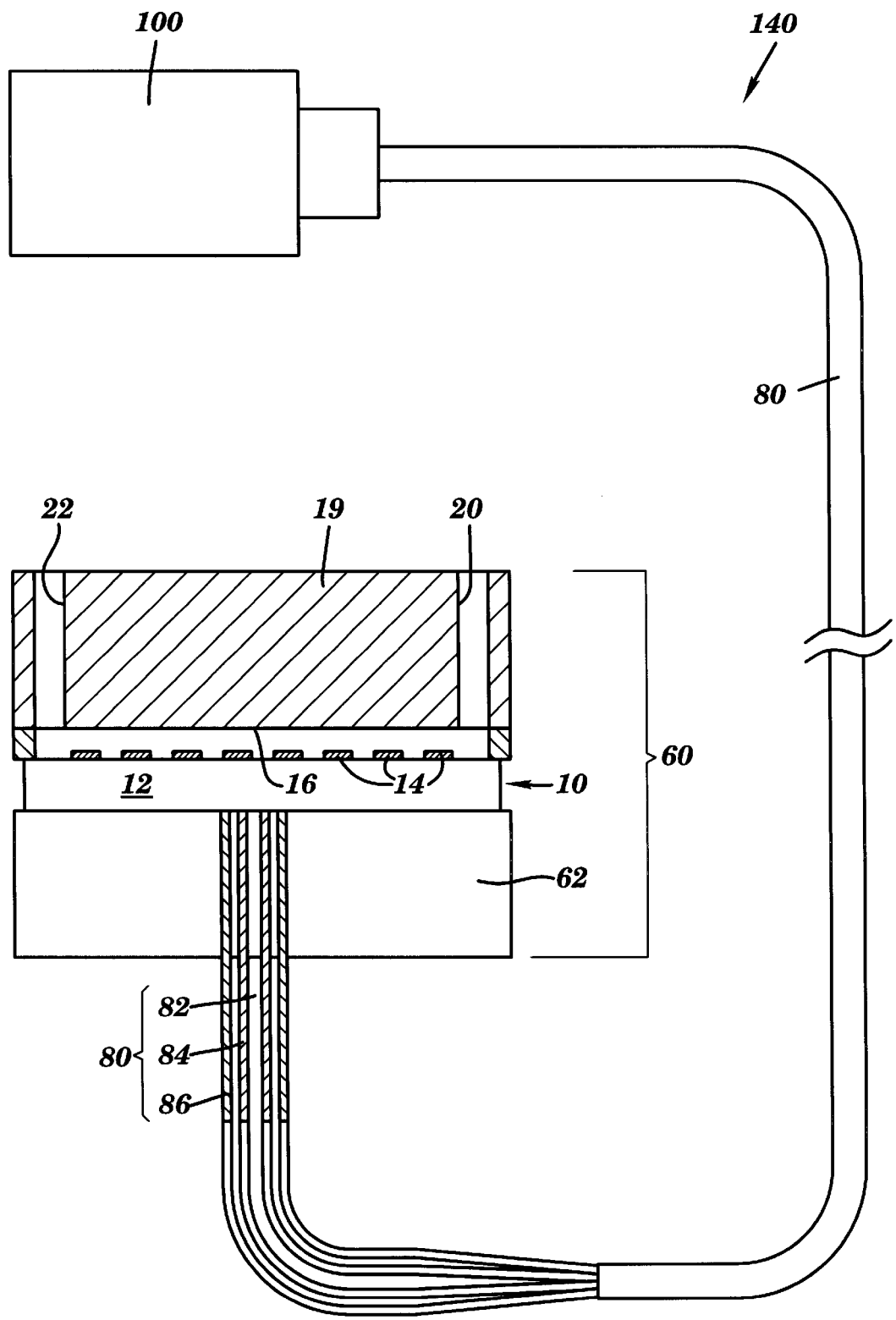
FIG. 5 is a schematic representation of a portion of a test apparatus capable of use in combination with an optical sensor of the present invention.

Alternatively, a test apparatus 140 as depicted in FIG. 5 may be utilized. Briefly described, such an apparatus 140 includes a flow cell assembly 60 and an excitation source and detector sub-system 100 such as that disclosed in U.S. patent application Ser. No. 08/617,714, and which is incorporated by reference in its entirety herein. Sub-system 100 emits a beam of light having a predetermined wavelength or spectral range. The light is directed through fiber optic cable 80 onto the surface of substrate web 10 directly opposite a stripe 14 in sample chamber 16. The light passes through the web, which, as mentioned hereinabove, is substantially transparent thereto, wherein the light is incident on a predetermined one of the sensor stripes 14. The incident light serves to excite a portion of sensor stripe 14. Stripe 14 then exhibits an optical response that corresponds to parameters (e.g. presence and/or concentration) of the predetermined analyte in the sample disposed in the sample chamber. This optical response is received by detector sub-system 100.

The calibration information for the optical sensor assembly is obtained by inserting a calibration sample or calibrant of known analyte composition into the sample chamber and measuring response of the sensor stripes thereto, in a manner substantially similar to testing an unknown sample.

Figure 6:
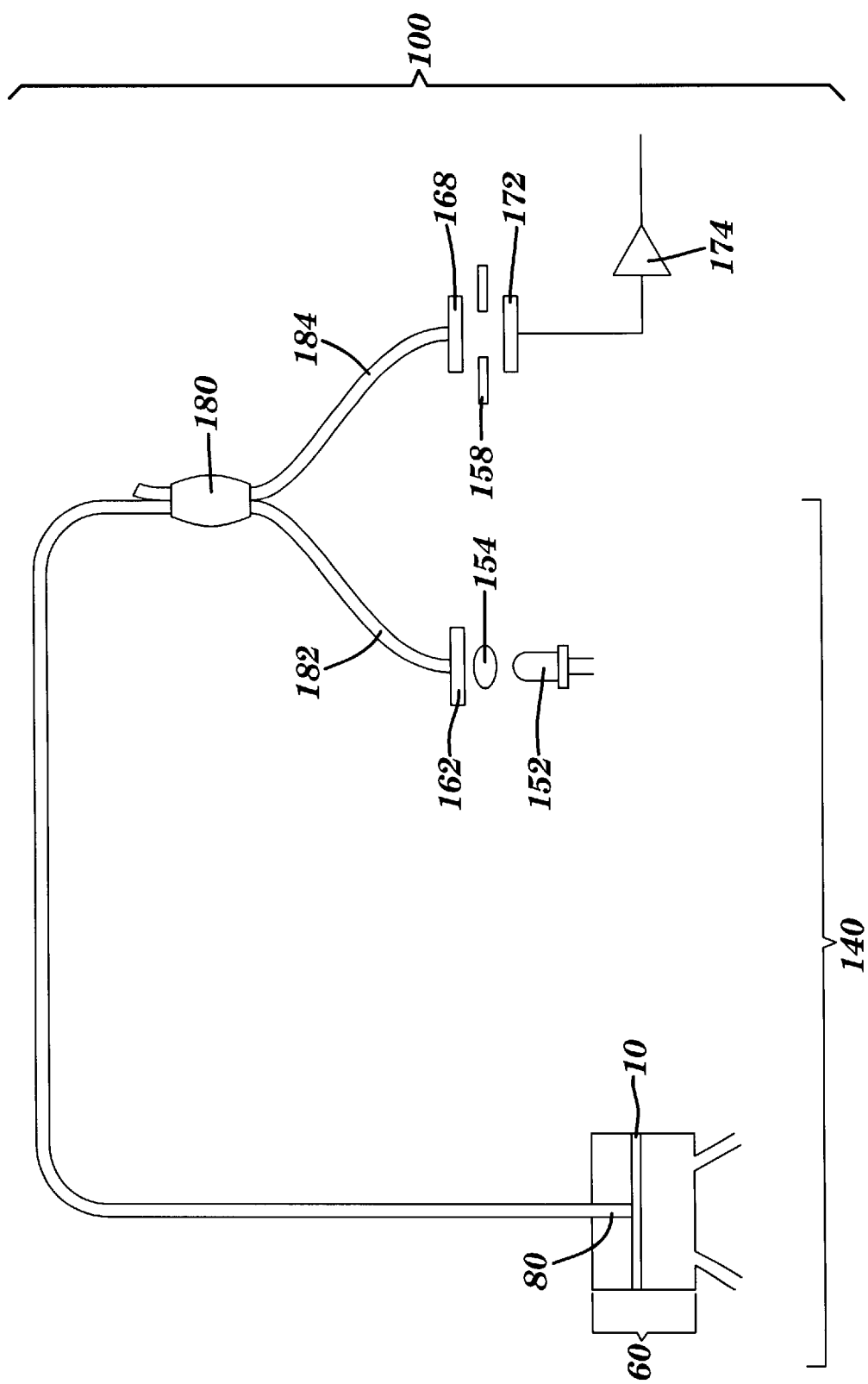
FIG. 6 is a schematic representation of a test apparatus including the portion thereof shown in FIG. 5, capable of measuring the output signal of a luminescent optical sensor of the present invention.

Referring now to FIGS. 5 and 6, test apparatus components 60 and 100 are described in additional detail. As shown in FIG. 5, flow cell assembly 60 is adapted to receive an optical sensor 10 for measurement. Radiation or light impinging upon substrate web 12 and emitted from stripe 14 is respectively guided to and from source and detection sub-system 100 by a fiber optic cable 80. Cable 80 includes a core 82, cladding 84 and sheath 86 where the core 82 and cladding 84 may be constructed from either glass or plastic polymer materials. Cable 80 is imbedded into base 62 which preferably has a low permeability to gases and a flat surface for contact with substrate 12. Base 62 may comprise stainless steel or another hard, thermally conductive material which is capable of assisting in controlling the temperature of membrane 14. Source radiation from cable 80 passes through substrate 12 and excites the luminescent dye molecules dispersed within membrane 14. Elongated member 19, including sample chamber 16, is pressed flat against optical sensor 10 as discussed hereinabove. Alternatively, optical sensor assembly 115 (FIG. 4), including sample chambers 116 (FIG. 4) may be utilized. Samples may be entered and subsequently removed through the entrance and exit apertures 20 and 22. The signal from each individual stripe 14 is then transmitted by cable 80 and returned to source and detector sub-system 100.

Referring to FIG. 6, the measurement apparatus 140 is comprised of flow cell assembly 60 and source and detector subsystem 100. For the optical source and detector subsystem 100 an LED source 152, and lens 154 are used to launch excitation light through filter 162 into one leg 182 of the fiber optic splitter 180 (available from American Laubscher Corp., Farmingdale, N.Y.). The luminescent or emitted light signal returning from the sensor 10 down fiber cable 80 and leg 184 is passed through filter 168 and aperture 158 before detection by photodiode 172. The output current of emission detector 172 is amplified with a preamplifier 174, such as a Stanford Research SR570 current preamplifier, converted to a voltage and recorded for use in analysis. For example, with the pH sensing dye fluorescein used in a sensor stripe, a Panasonic® Blue LED(P389ND available from Digikey, Theif River Falls, Minn.) would be preferred for source 152. A 485 nm center wavelength 22 nm half bandwidth filter (available from Omega Optical, Brattleboro, Vt.) would be preferred for filter 162 and a 535 nm center wavelength 35 nm half bandwidth filter, also available from Omega Optical, Brattleboro, Vt. would be preferred for filter 168. It should also be evident that each individual sensor stripe, employing a different dye, will require its own preferred LED source 152, excitation interference filter 162 and emission interference filter 168. While particular arrangements of optical source and detection systems have been disclosed herein, other equivalent instruments are known to those skilled in the art and are intended to be within the scope of the present invention.

Testing procedures are undertaken at each sensor stripe 14 in sample chamber 16, either sequentially or in parallel, to test for all of the predetermined analytes. Once analysis is complete, the pump means removes the sample from chamber 16 through exit aperture 22.

Analysis of subsequent samples, as well as the aforementioned analysis of a calibration sample, may be accomplished in a manner common to prior art sensors. Namely, sample chamber 16 may be flushed with wash fluid to remove traces of the previous sample from the sample chamber and sensor stripes. Sample chamber 16 and the same discrete portions of sample stripes 14 with which the sample chamber is superposed, may be re-used for a subsequent test sample. In this manner, sensor assembly 15 may function as a conventional 'multiple use' device. Alternatively the present invention includes use of optical sensor 10 as a 'multiple single use device' in which subsequent tests may be performed at discrete unused portions of sensor stripes 14. In this regard, after testing is completed, sample chamber 16 may be washed and dried sufficiently to clear any sample traces from chamber member 19 and prevent liquid carryover to the next chosen position. Sample chamber 16 may then be moved relative the length of optical sensor 10 to superimpose cavity 18 with an unused portion of sensor stripes 14. Once so disposed, a subsequent sample may be fed into sample chamber 16 for analyte analysis. These steps may be reiterated, so that a fresh discrete portion of each sensor stripe 14 is used for each sample (calibrant or unknown) in either a sequential or simultaneous manner.

However, the present invention is preferably used in the 'multiple single use' mode when it is combined with provisions for a plurality of sample chambers 116, as shown in FIG. 4, to enable each sample chamber to be used only once. This nominally eliminates the need for washing operations and each sample chamber effectively becomes a waste container for its own sample. In addition, this aspect substantially eliminates the potential for cross-contamination of samples occasioned by repeated use of sample chambers, as mentioned hereinabove.

An additional advantage of this construction is the ability to conduct parallel testing of unknown and calibration samples. In this regard, sample chambers 116 disposed proximate, and preferably adjacent, one another may be utilized for simultaneously testing calibration samples and unknown samples. Such parallel, simultaneous testing provides additional precision in testing not available with prior art devices by effectively eliminating any inaccuracies in sensor response occasioned by temporal variations between tests of calibration and unknown samples.

Moreover, in a further variation, both sensor assembly 15 (FIG. 2) and sensor assembly 115 (FIG. 4) may be calibrated at multiple discrete positions along the lengths of sensor stripes 14. This advantageously provides additional data points for increased precision of the calibration information. In this regard, for still further precision, calibration samples may be tested in chambers disposed on opposite sides of, and adjacent to, a sample chamber containing an unknown sample.

This multiple position calibration also facilitates utilization of discrete calibration samples having different combinations of analytes disposed therein. This aspect tends to enhance the stability of the individual calibration mixtures by enabling separation of analytes, such as, for example, glucose and oxygen. One skilled in the art will recognize that the presence of oxygen in a glucose solution tends to favor oxidative microorganism growth. Thus, it is advantageous to have separate oxygen and glucose calibration solutions. In general, a first calibration sample may be provided with a first predetermined combination of analytes, and a second calibration sample provided with a second predetermined combination of analytes. The first and second calibration samples then may be tested simultaneously at discrete positions of sensor stripes 14. The data obtained from testing these separate calibration samples may be combined for analyzing test results for unknown samples at the same or other discrete positions along sensor stripes 14.

Thus, as discussed hereinabove, rather than rely on temporal stability, the present invention relies on spatial stability, namely the assumption that sensor portions located proximate one another along the sensor stripes will exhibit substantially identical response characteristics. This reliance is made possible by the deposition of the analytical elements as substantially continuous sensor stripes 14 as discussed hereinabove, with increased precision enabled, as desired, through the use of adjacent sample chambers 116 for respective testing and calibration.

Moreover, the combination of spatial and temporal proximity in these measurements permits the use of conventional differential and ratiometric techniques to further improve accuracy and precision thereof. In particular, by introducing and measuring an unknown sample and a calibrant into respective sample chambers at the same time, it is possible to simultaneously observe and compare the response dynamics of the calibrant versus the unknown sample to further enhance accuracy of response measurement.

The construction of the present invention also addresses the problem of storage history variations that tend to compromise performance and consistency of prior art sensors. For example, otherwise identical prior art sensors may have been stored for different periods of time or exposed to variations in environmental conditions (e.g. differences in temperature, humidity or radiation) during storage, that may impact consistency between sensors. By virtue of fabricating the analytical elements as nominally continuous stripes on a single substrate, the present invention tends to ensure that each discrete portion of sensor stripes 14 has an identical storage history to further improve sensor consistency.

Moreover, the present invention, particularly sensor assembly 115, provides an additional advantage in terms of waste reduction. As mentioned hereinabove, approximately 80% of waste in connection with prior art sensors comprises wash fluid used to clean the sample chamber and analytical elements between unknown samples. Such waste is generally classified as biohazardous, thus requiring relatively rigorous and expensive special handling. By substantially reducing or eliminating the washing requirements through the construction of individualized sample chambers 116 as discussed hereinabove, the present invention effectively reduces biohazardous waste relative to prior art devices, for desireable cost and safety improvements.

The following illustrative examples are intended to demonstrate certain aspects of the present invention. It is to be understood that these examples should not be construed as limiting. In the examples, sensor stripes 14 were deposited on a 75 micrometers (m) thick Mylar® substrate web 12 positioned with an IVEK LS Table. Deposition of the polymer and dye formulations was achieved with a micro dispensing system of the type discussed hereinabove. Examples of the construction of striped sensor membranes and demonstrations of their functionality are given in the following:

EXAMPLE 1

Into one ml of the solvent tetrahydrafuran (THF) from Alrich (Milwaukee, Wis.) were dissolved 100 mg of polystyrene (MW=280,000 and obtained from Scientific Polymer Products Inc. in Ontario, N.Y.) and 2 mg of the oxygen sensing dye octaethyl-Pt-porphyrin ketone (OEPK) purchased from the Joanneum Research Institute in Graz Austria. The viscosity of the solution was 37 centipoise (cps) as measured on a Brookfield RVDVIIIC/P Rheometer. The mixture was then deposited through a nozzle located 75 m above a clear Mylar® film and at a rate of 5 ml/sec with a Digispense 2000 pump system from IVEK to produce a stripe at a linear rate of 50 mm/sec, having a width of approximately 2 mm and a thickness of about 5 m when dried. After air drying, the stripes were cured at 110° C. for one hour under a vacuum and cooled to remove all traces of solvent. The resultant oxygen sensing stripes were translucent and of a light purple color.

EXAMPLE 2

Figure 7A:
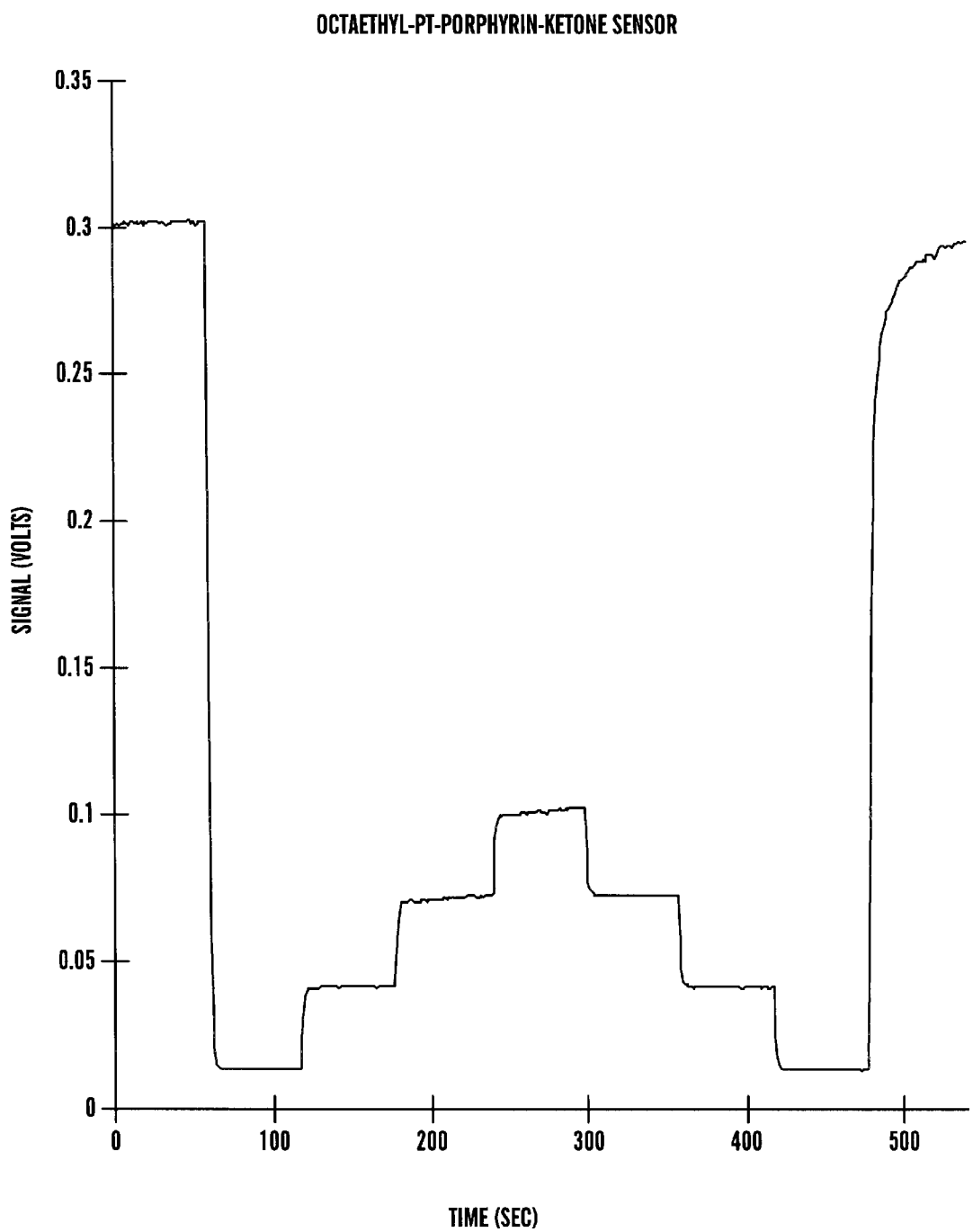
FIG. 7A is a graphical representation of optical response of a portion of an optical oxygen sensor of the type shown in FIGS. 1 and 4.
Figure 7B:
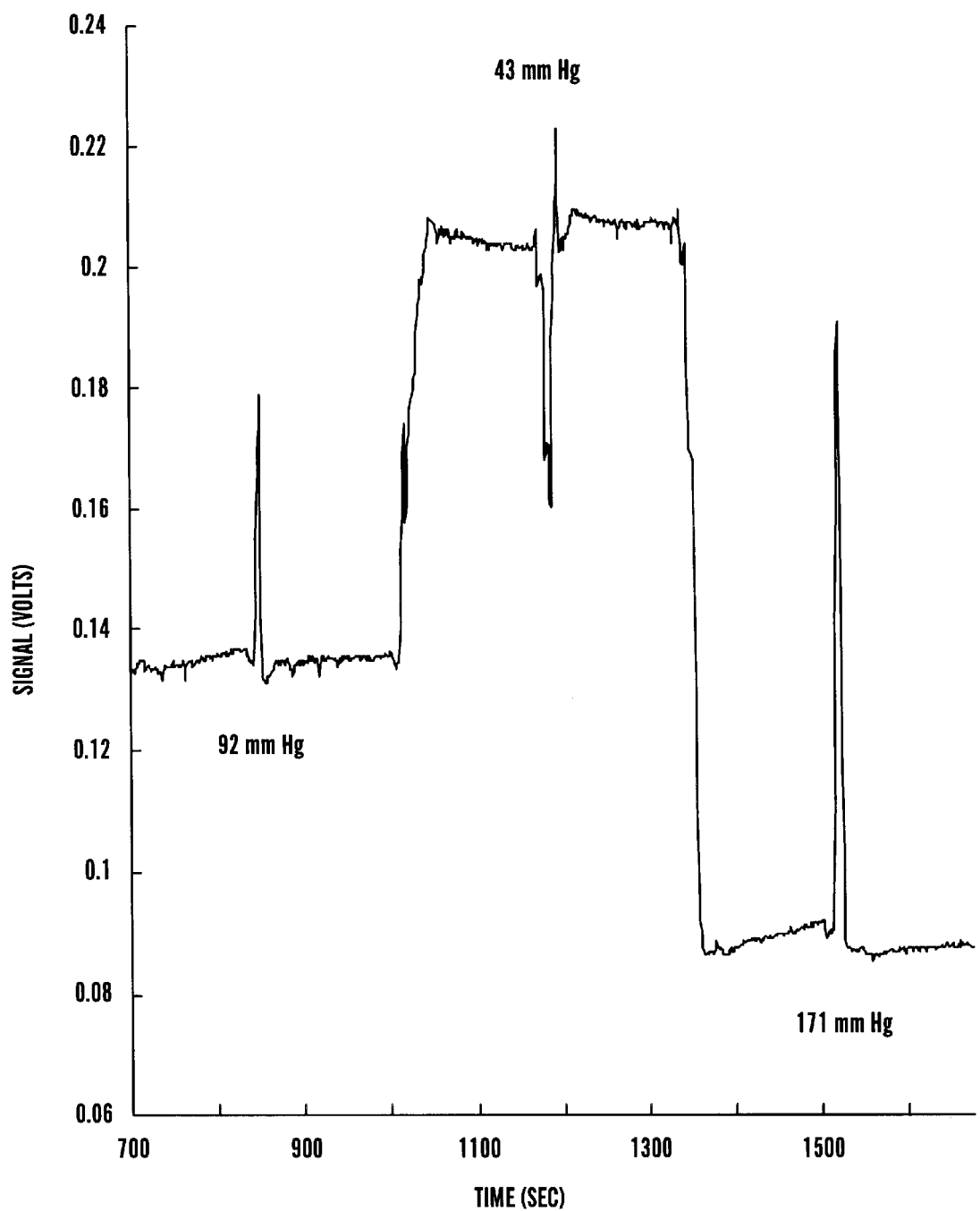
FIG. 7B is a graphical representation of response to aqueous buffer samples, of the portion of the optical oxygen sensor utilized to generate FIG. 7A.

A sensor stripe from example 1 was placed in the measurement device described with respect to FIG. 5 but altered to contain the appropriate yellow LED source, an Omega 585DF20 excitation filter, and a Omega 750DF50 emission filter for the dye octaethyl-Pt-porphyrin ketone. A flowing gas stream with differing partial pressures of oxygen corresponding to 0%, 100%, 26%, 12%, 7%, 12%, 26%, 100% and finally 0% oxygen was passed over the sensor and the luminescence elicited from the dye recorded. The luminescence quenching trace in FIG. 7A was used to derive a Stern-Volmer quenching constant of 0.026 $(mmHg)^{-1}$. The exposure of the striped oxygen sensing membrane to duplicate aqueous buffer samples tonometered to partial pressures of 92, 43 and 171 mm Hg oxygen also produced rapid, and reversible responses as documented in FIG. 7B which could be used to quantitate the amount of dissolved oxygen in solution.

EXAMPLE 3

A sensing stripe for the analyte oxygen was constructed as follows. The dye octaethyl-Pt-porphyrin was synthesized according to methods described in J. Molecular Spectroscopy 35:3 p359–375 (1970). The styrene/acrylonitrile copolymer, with MW=165,000 and containing 25% acrylonitrile, was obtained from Scientific Polymer Products Inc., Ontario, N.Y. A mixture of 2 mg dye and 100 mg of copolymer dissolved into 1 ml of THF was deposited on a Mylar® film as in example 1.

EXAMPLE 4

Figure 8:
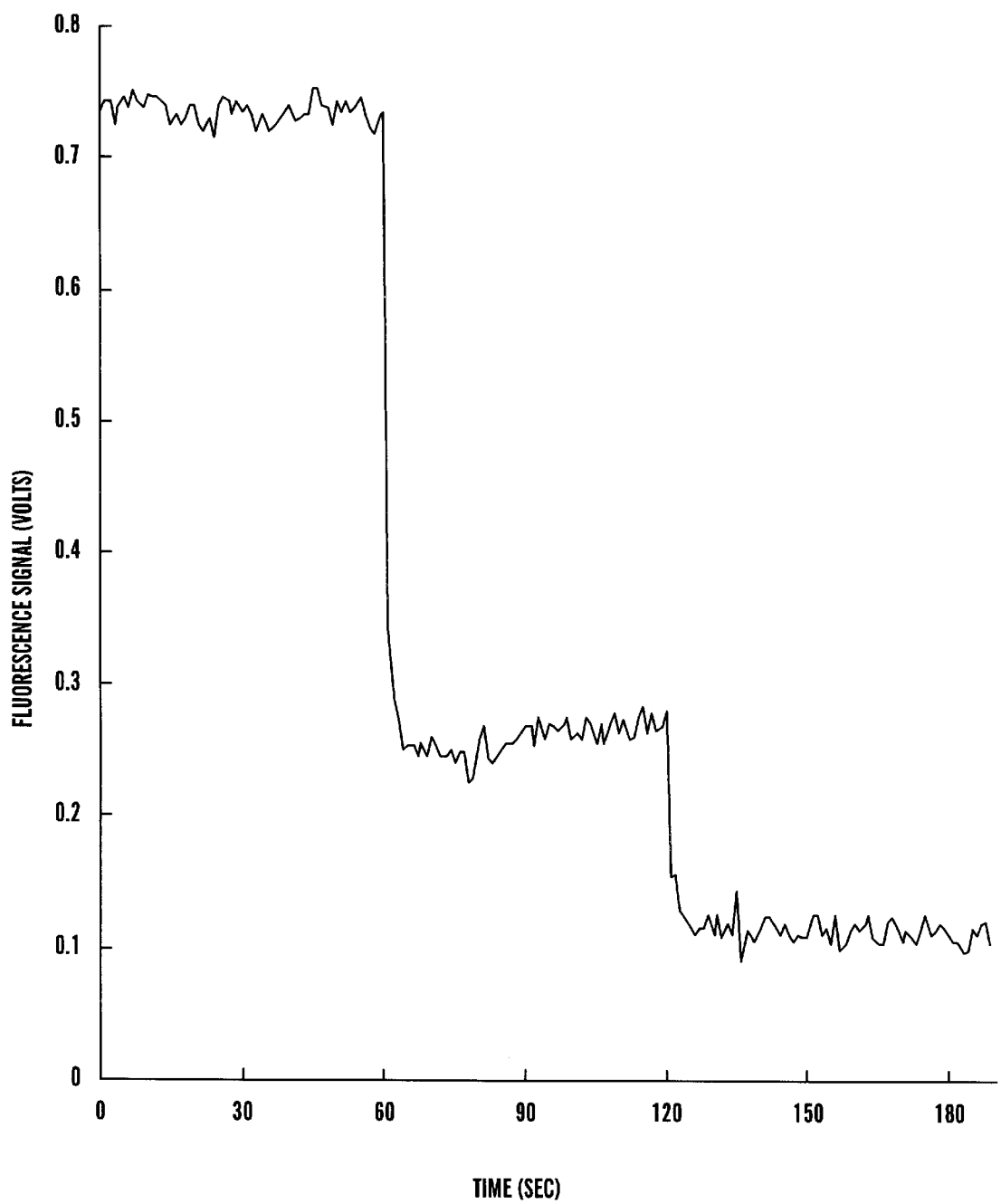
FIG. 8 is a graphical representation of the response of an optical oxygen sensor of the type shown in FIGS. 1 and 4 and constructed from a second different membrane and dye formulation.

A sensor stripe from example 3 was placed in the measurement device described hereinabove with respect to FIG. 5 and a flowing gas stream with differing partial pressures of oxygen corresponding to 0%, 26% and finally 100% oxygen were passed over the sensor. The luminescence elicited with green 540 nm excitation light from the octaethyl-Pt-porphyrin dye was continuously measured at 650 nm and the luminescence quenching trace recorded as shown in FIG. 8.

EXAMPLE 5

An analytical element for $CO_2$ was fabricated substantially as set forth in the above-referenced '525 and '148 patents. Namely, a 7% solution (by weight) of ethyl cellulose was prepared by dissolving 7 g in 100 ml of a 7:3 toluene:ethanol mixture. To this solution was added 5 mg of hydroxpyrenetrisulponic acid (HPTS). 2 ml of Tetrabutylamonium hydroxide was added to the mixture. The solution striped at a linear rate of 50 mm/sec with a solution delivery rate of 5 ml/sec with the nozzle located 75 m above the substrate. After air drying overnight this produced very faintly green stripes for $CO_2$ sensing.

EXAMPLE 6

A portion of the striped $CO_2$ sensor in example 5 was placed in an optical chamber on a Perkin Elmer LS-50B spectrofluorimeter. Front surface illumination and collection optics permitted transmission of the 460 nm excitation and 506 nm emission signals through the Mylar® substrate. Tonometered liquid samples were introduced into a hollowed out aluminum sample chamber with an opening covered by the sensor stripe. Introduction of increasing partial pressures of $CO_2$ corresponding to 5.66 and 8.33% $CO_2$ caused reversible fluorescence changes as documented in FIG. 9.

EXAMPLE 7

Fifty mg of a pH sensitive copolymer composed of N,N-Dimethylacrylamide and N-tert-butylacrylamide monomers with a covalently linked 4-acrylamidofluorescein was dissolved into 1 ml of THF in the manner described by Alder et al. in the above-referenced patent application WO 95/30148. The polymer solution was striped at a speed of 50 mm/sec and dispensed at a rate of 4 ml/sec from a nozzle head located 100 m above the Mylar® film. After solvent evaporation the stripes were virtually colorless until wetted when they became faint green with a basic aqueous sample for measurement.

EXAMPLE 8

A striped pH sensor constructed as in Example 7 was further placed in the sampling device and measured with the Perkin Elmer LS50-B in a manner similar to that described in example 6. In this case, the excitation wavelength was set to 485 nm and emission recorded at 530 nm while consecutive buffer samples corresponded to pH 7.5, 7.1, 6.8, 7.1, and 7.5 were introduced to the sensor. The reversible fluorescence quenching due to acidification of the fluorescein sensor dye by the samples is as recorded in FIG. 10.

EXAMPLE 9

Figure 11:
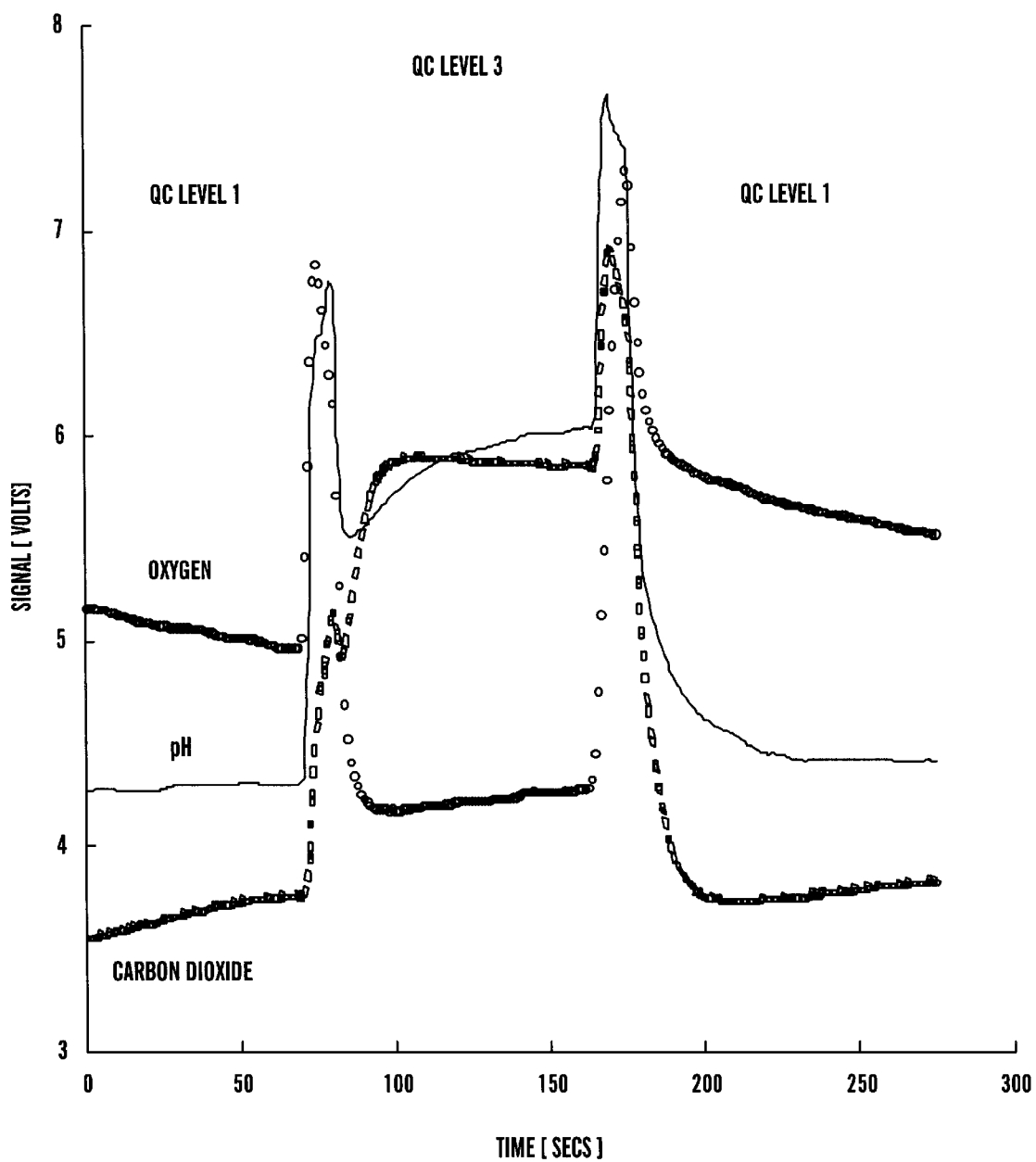
FIG. 11 is a graphical representation of the simultaneous response of sensors of the present invention, for three analytes, for three different known samples.

Using striping methods as described in examples 3,5 and 7, a series of parallel sensor stripes for oxygen, carbon dioxide and pH were laid down on a Mylar® film similar to that illustrated in FIG. 1. A 150 m thick film of Mylar® with double sided adhesive backing giving a total thickness of 210 m was punched with a series of parallel cutouts transverse to the longitudinal direction of the film to form intermediate web 26. This intermediate web was then fixed to a clear film of Mylar® to form cover web 28, and a series of holes punched, one at each end of the parallel cutouts. In the final assembly step, the film containing the sensor stripes was placed as the last sandwich layer on the bottom with the sensor side in contact with the transverse cutouts on the intermediate layer as shown in FIG. 4, thus forming sample chambers 118 approximately 210 m deep. For measurements and analyte determinations, this sensor assembly was subsequently placed in an instrument having several fiber optic splitter assemblies arranged in parallel with the sample chambers. The appropriate color excitation and collection optic was located directly below the corresponding stripe to be measured as indicated in FIG. 5. As the assembly containing the sensor stripes and sample chambers was moved along, a bar containing an inlet and exit port was clamped over the portal holes in the top clear Mylar® film (cover web 28) and an individual sample chamber was filled with a single calibrant or sample. For demonstration purposes, ampuled vials of the Certain® Plus standards by Chiron Diagnostics served as both calibrants and samples with known values. These were opened and aspirated into the sample wells over the sensor stripes. The values for level 1 corresponded to pH 7.151, pCO2 68.9 mmHg and pO2 69.0 mmHg. The values for level 3 corresponded to pH 7.409, pCO2 40.1 mmHg and pO2 104.5 mmHg. The simultaneous response of the sensors to a change in calibrant is illustrated in FIG. 11.

EXAMPLE 10

Figure 12:
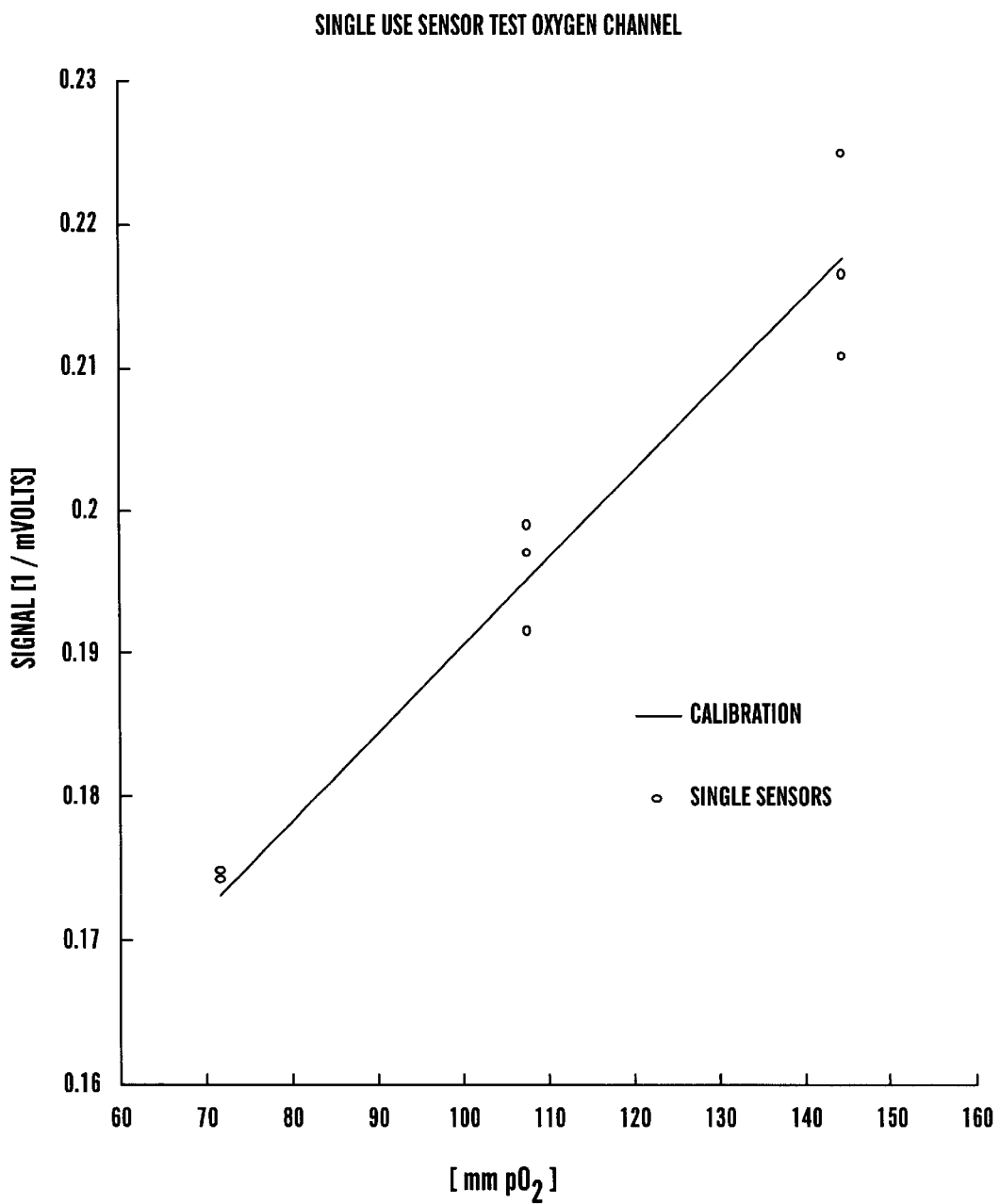
FIG. 12 is a graphical response curve for a single oxygen sensor stripe of the present invention calibrated by the use of several known samples similar to those utilized to generate FIG. 11.

Using the sensor format and methodology described in example 9, a standard response curve was obtained for a single sensor calibrated by three known Certain® Plus standards corresponding to 71.6, 107.7 and 144.5 mm Hg oxygen and is represented by the solid line shown in FIG. 12. The optical sensor assembly was then advanced to a new position and another different but known sample aspirated onto a fresh position on each sensor stripe. These are represented by the single sensor point responses. Table 1 shows a comparison of the measured values calculated using the calibration algorithm. Although the calibration was performed for one sensor, the algorithm was applied to separate individual sensor positions along the stripe, each with only a single measurement.

TABLE 1

| Actual Level pO$_2$ (mmHg) | 71.6 | 107.7 | 144.5 |
|---|---|---|---|
| Measured Values with | 73.4 | 113.9 | 142.6 |
| Individual Sensors | 74.3 | 110.6 | 133.1 |
|  |  | 101.8 | 156.3 |
| Average | 73.9 | 107.3 | 144.0 |

The foregoing description is intended primarily for purposes of illustration. Although the invention has been shown and described with respect to an exemplary embodiment thereof, it should be understood by those skilled in the art that the foregoing and various other changes, omissions, and additions in the form and detail thereof may be made therein without departing from the spirit and scope of the invention.

Having thus described the invention, what is claimed is:

1. An optical sensor assembly adapted for sensing analyte content of a plurality of samples, said optical sensor assembly comprising:
   (a) an optical sensor comprising:
      a substrate web of predetermined length, said substrate web being substantially gas impermeable and optically transparent in a predetermined spectral range;
      a plurality of elongated sensor stripes extending in parallel, spaced relation along the length of said web;
      each one of said plurality of sensor stripes adapted for providing an optically discernible response to presence of at least one analyte;
      said optical sensor adapted for selective analyte-sensing contact with the plurality of samples, wherein each one of the plurality of samples are selectively superimposable with each one of said plurality of elongated sensor stripes at one a plurality of discrete sample positioned along the lengths thereof;
      said optically discernible response being substantially identical at said plurality of discrete sample positions; and
   (b) at least one sample chamber superimposable with each of said plurality of elongated sensor stripes at one of said plurality of discrete sample positions along the lengths thereof;
   wherein said at least one sample chamber is adapted for alternately maintaining individual ones of the plurality of samples in said analyte-sensing contact, and wherein said at least one sample chamber comprises:
      an elongated cavity disposed within a chamber member, said elongated cavity being defined by a substantially concave surface of said chamber member;
      said elongated cavity including first and second apertures disposed at opposite ends thereof to facilitate alternate entry and exit of the individual ones of the plurality of samples to and from said sample chamber;
      said chamber member adapted to extend across said plurality of sensor stripes with said substantially concave surface facing said web, wherein said optical sensor effectively closes said substantially concave surface to define a longitudinal side wall of said elongated cavity.

2. The optical sensor assembly as set forth in claim 1, further comprising a plurality of said sample chambers.

3. The optical sensor assembly as set forth in claim 1, wherein said at least one sample chamber is moveable for selective superimposition with said plurality of discrete sample positions along the lengths of said sensor stripes.

4. The optical sensor assembly as set forth in claim 3, wherein said at least one sample chamber is adapted to extend orthogonally to each of said plurality of elongated sensor stripes.

5. An optical sensor assembly adapted for sensing analyte content of a plurality of samples, said optical sensor assembly comprising:
   (a) an optical sensor comprising:
      a substrate web of predetermined length, said substrate web being substantially gas impermeable and optically transparent in a predetermined spectral range;
      a plurality of elongated sensor stripes extending in parallel, spaced relation along the length of said web;
      each one of said plurality of sensor stripes adapted for providing an optically discernible response to presence of at least one analyte;
      said optical sensor adapted for selective analyte-sensing contact with the plurality of samples, wherein each one of the plurality of samples are selectively superimposable with each one of said plurality of elongated sensor stripes at one of a plurality of discrete sample positioned along the lengths thereof;
      said optically discernible response being substantially identical at said plurality of discrete sample positions; and
   (b) a plurality of sample chambers disposed in parallel, spaced relation on said web, each one of said plurality of sample chambers being sealably superposed with said plurality of elongated sensor stripes at one of said plurality of discrete sample positions along the lengths thereof,
   wherein each of said plurality of sample chambers is adapted for alternately maintaining individual ones of the plurality of samples in said analyte-sensing contact.

6. The optical sensor as set forth in claim 5, wherein the plurality of samples comprises at least one unknown sample and at least one calibration sample, said optical sensor adapted for being calibrated upon disposition of the calibration sample in one of said sample chambers distinct from an other sample chamber adapted to receive said at least one unknown sample.

7. The optical sensor assembly as set forth in claim 5, wherein each of said plurality of sample chambers comprises:
   an elongated cavity disposed within a chamber member, said elongated cavity being defined by a substantially concave surface of said chamber member;
   said elongated cavity including first and second apertures disposed at opposite ends thereof to facilitate alternate entry and exit of at least an individual one of the plurality of samples to and from said sample chamber;
   said chamber member sealably superposed with said substrate web and said plurality of sensor stripes, wherein a discrete portion of said optical sensor effectively closes said substantially concave surface to define a longitudinal side wall of said elongated cavity.

8. The optical sensor assembly as set forth in claim 7, wherein said chamber member further comprises:
- a chamber web sealably superposed with said substrate web and said sensor stripes;
- a cover web sealably superposed with said chamber web;
- said chamber web having a plurality of slots extending in spaced parallel relation across said sensor stripes;
- wherein each said slot and each portion of said cover web superposed therewith define said concave surface.

9. The optical sensor assembly as set forth in claim 8, wherein said entry and exit apertures are disposed in said cover web.

10. The optical sensor assembly as set forth in claim 8, wherein said entry and exit apertures are disposed in said substrate web.

11. The optical sensor assembly as set forth in claim 8, wherein at least one of said entry and exit apertures is disposed in said substrate web and at least one of said entry and exit apertures is disposed in said cover web.

12. The optical sensor assembly as set forth in claim 7, wherein said plurality of sample chambers are disposed in fixed relation on said optical sensor.

* * * * *